Figure 1:
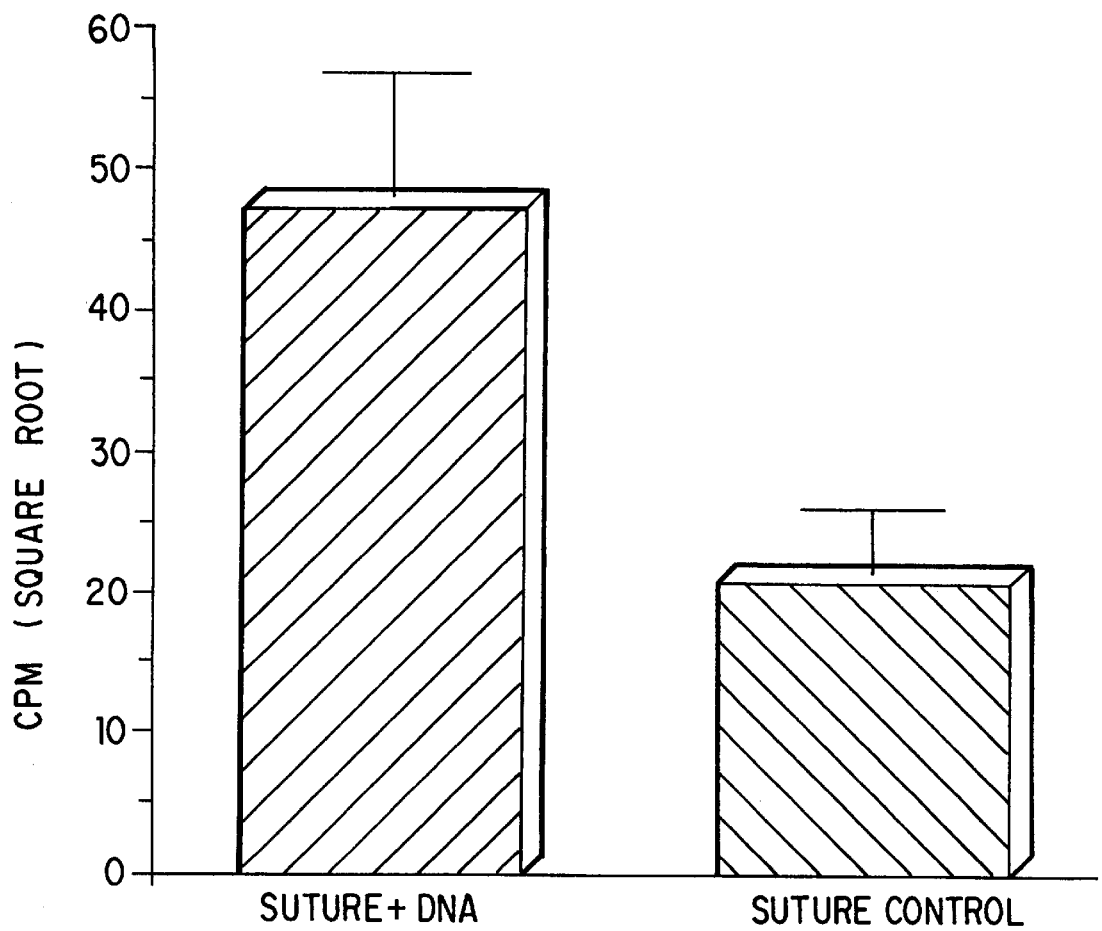

US006143037A

United States Patent [19]
Goldstein et al.

[11] Patent Number: 6,143,037
[45] Date of Patent: *Nov. 7, 2000

[54] COMPOSITIONS AND METHODS FOR COATING MEDICAL DEVICES

[75] Inventors: Steven Goldstein; Robert J. Levy; Vinod Labhasetwar; Jeffrey F. Bonadio, all of Ann Arbor, Mich.

[73] Assignee: The Regents of the University of Michigan, Ann Arbor, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/662,341

[22] Filed: Jun. 12, 1996

[51] Int. Cl.$^7$ .......................................................... A61F 2/54
[52] U.S. Cl. ................................ 623/66; 427/21; 514/44; 435/6
[58] Field of Search .................................. 427/2.1; 514/2, 514/44; 604/890.1, 4, 891.1; 128/898; 623/66; 435/6; 424/422

[56] References Cited

U.S. PATENT DOCUMENTS

| | | | |
|---|---|---|---|
| 3,277,033 | 10/1966 | Ugi ............................................. | 525/153 |
| 3,557,795 | 1/1971 | Hirsch . | |
| 3,839,297 | 10/1974 | Wasserman et al. ..................... | 528/357 |
| 4,024,871 | 5/1977 | Stephenson . | |
| 4,433,688 | 2/1984 | Bichon . | |
| 4,532,929 | 8/1985 | Mattei et al. . | |
| 4,534,958 | 8/1985 | Adams et al. ............................. | 424/45 |
| 4,563,489 | 1/1986 | Urist . | |
| 4,649,920 | 3/1987 | Rhum . | |
| 4,711,241 | 12/1987 | Lehmann . | |
| 4,844,067 | 7/1989 | Ikada et al. . | |
| 4,857,602 | 8/1989 | Casey et al. . | |
| 4,898,734 | 2/1990 | Mathiowitz et al. . | |

(List continued on next page.)

FOREIGN PATENT DOCUMENTS

| | | |
|---|---|---|
| 0 190 833 A2 | 8/1986 | European Pat. Off. . |
| 0 335 972 A1 | 10/1989 | European Pat. Off. . |
| 0 336 964 A1 | 10/1989 | European Pat. Off. . |
| 0 407 580 A1 | 1/1991 | European Pat. Off. . |
| 0 529 711 A1 | 3/1993 | European Pat. Off. . |
| 2 649 321 | 1/1991 | France . |
| WO 90/10034 | 9/1990 | WIPO . |
| WO 91/06286 | 5/1991 | WIPO . |
| WO 91/06287 | 5/1991 | WIPO . |
| WO 91/15193 | 10/1991 | WIPO . |
| WO 92/17165 | 10/1992 | WIPO . |
| WO 92/17167 | 10/1992 | WIPO . |
| WO 93/00076 | 1/1993 | WIPO . |

(List continued on next page.)

OTHER PUBLICATIONS

Douglas et al., 1986, "Poly(butyl 2–cyanoacrylate) Nanoparticles with Differing Surface Charges," *Journal of Controlled Release* 3:15–23.

Gref et al., 1994, "Biodegradable Long–Circulating Polymeric Nanospheres," *Science* 263:1600–1603.

Kreuter, 1988, "Possibilities of using nanoparticles as carriers for drugs and vaccines," *J. Microencapsulation* 5(2):115–127.

Niwa et al., 1993, "Preparations of biodegradable nanospheres of water–soluble and insoluble drugs with D,L–lactide/glycolide copolymer by a novel spontaneous emulsification solvent diffusion method, and the drug release behavior," *Journal of Controlled Release* 25:89–98.

(List continued on next page.)

Primary Examiner—Mickey Yu
Assistant Examiner—Kelly O'Hara
Attorney, Agent, or Firm—Pennie & Edmonds LLP

[57] ABSTRACT

Compositions and methods for coating medical devices with pharmaceutical agents and devices coated with the compositions. The coated devices provide controlled or sustained release of pharmaceutical agents for the treatment of wounds or disease.

8 Claims, 7 Drawing Sheets

— 100 μm

U.S. PATENT DOCUMENTS

| | | |
|---|---|---|
| 4,952,419 | 8/1990 | De Leon et al. . |
| 4,968,350 | 11/1990 | Bindschaedler et al. . |
| 4,983,180 | 1/1991 | Kawai et al. . |
| 5,032,638 | 7/1991 | Wang et al. . |
| 5,100,433 | 3/1992 | Bezwada et al. . |
| 5,102,402 | 4/1992 | Dror et al. . |
| 5,102,420 | 4/1992 | Hunter et al. . |
| 5,123,912 | 6/1992 | Kaplan et al. . |
| 5,147,383 | 9/1992 | Bezwada et al. . |
| 5,225,279 | 7/1993 | Redlich et al. . |
| 5,258,436 | 11/1993 | Wheatley et al. . |
| 5,271,961 | 12/1993 | Mathiowitz et al. . |
| 5,292,522 | 3/1994 | Petereit et al. . |
| 5,298,422 | 3/1994 | Schwartz et al. . |
| 5,304,121 | 4/1994 | Sahatjian . |
| 5,312,437 | 5/1994 | Hermes et al. . |
| 5,324,775 | 6/1994 | Rhee et al. . |
| 5,378,451 | 1/1995 | Gorman et al. ............ 424/47 |
| 5,378,540 | 1/1995 | Olson . |
| 5,460,831 | 10/1995 | Kossovksy et al. . |
| 5,464,650 | 11/1995 | Berg et al. . |
| 5,470,829 | 11/1995 | Prissell et al. . |
| 5,474,797 | 12/1995 | Sioshansi et al. . |
| 5,478,564 | 12/1995 | Wantier et al. . |
| 5,480,411 | 1/1996 | Liu et al. . |
| 5,480,656 | 1/1996 | Okada et al. . |
| 5,480,868 | 1/1996 | Kamei et al. . |
| 5,480,963 | 1/1996 | Jiang et al. . |
| 5,514,550 | 5/1996 | Findlay et al. ............. 435/6 |
| 5,545,135 | 8/1996 | Iacob et al. . |
| 5,563,056 | 10/1996 | Swan et al. . |
| 5,593,974 | 1/1997 | Rosenberg et al. . |
| 5,674,192 | 10/1997 | Sahatjian et al. . |
| 5,674,703 | 10/1997 | Woo et al. . |
| 5,698,531 | 12/1997 | Nabel et al. . |
| 5,707,969 | 1/1998 | Nabel et al. . |
| 5,723,119 | 3/1998 | Schwartz et al. . |
| 5,770,580 | 6/1998 | Ledley et al. . |
| 5,962,427 | 10/1999 | Goldstein et al. . |

FOREIGN PATENT DOCUMENTS

| | | |
|---|---|---|
| WO 93/21906 | 11/1993 | WIPO . |
| WO 93/21969 | 11/1993 | WIPO . |
| WO 94/18955 | 9/1994 | WIPO . |
| WO 94/23699 | 10/1994 | WIPO . |
| WO 95/22963 | 8/1995 | WIPO . |
| WO 95/24929 | 9/1995 | WIPO . |
| WO 96/11671 | 4/1996 | WIPO . |

OTHER PUBLICATIONS

Scholes et al., 1993, "The preparation of sub–200 nm poly(lactide–co–glycolide) microspheres for site–specific drug delivery," *Journal of Controlled Release* 25:145–153.

Di Silvio, et al. "The Use of Gelatin as a Vehicle for Drug and Peptide Delivery." J Mater Sci Mater Med 5(11):819–24, 1994.

Bindschaedler et al., 1986, "Osmotically Controlled Drug Delivery Systems Produced From Organic Solutions and Aqueous Dispersions of Cellulose Acetate," *Journal of Controlled Release* 4:203–212.

Allémann et al., 1992, "Preparation of Aqueous Polymeric Nanodispersions by a Reversible Salting–Out Process: Influence of Process Parameters on Particle Size," *Int. J. Pharm.* 87:247–253.

Schwab et al., 1994, "Antisense Oligonucleotides Adsorbed to Polyalkylcyanoacrylate Nanoparticles Specifically Inhibit Mutated Ha–ras–mediated Cell Proliferation and Tumorigenicity in Nude Mice," *Proc. Natl. Acad. Sci. U.S.A.* 91:10460–10464.

Di Silvio et al., 1994, "The Use of Gelatin As a Vehicle For Drug and Peptide Delivery," Chapman & Hall: 819–823.

Valere et al., 1995, "Continuous Secretion of Human Soluble CD4 in Mice Transplanted With Genetically Modified Cells," *Gene Therapy* 2:197–202.

———— 100 μm

———— 100 μm

— 10μm

— 10μm

COMPOSITIONS AND METHODS FOR COATING MEDICAL DEVICES

1. INTRODUCTION

The present invention relates to compositions for coating medical devices with a polymeric matrix containing pharmaceutical agents, methods for coating the medical devices and medical devices coated therewith. The coated devices are useful for targeted local delivery of pharmaceutical agents at a site of medical intervention for the treatment of wounds and disease.

2. BACKGROUND OF THE INVENTION

The desirability of coating medical devices such as, inter alia, surgical implants, sutures and wound dressings with pharmaceutical agents is well documented in the art. Such coated devices could theoretically provide a means for locally delivering pharmaceutical or therapeutic agents at the site of medical intervention to treat a variety of diseases. For example, surgical implants or sutures coated with antibiotics can provide local delivery of antibiotic directly at an implantation or suture site, thereby decreasing the onset of infection following the surgical intervention.

Polymer compositions and methods for coating implants, especially sutures, are well-known in the art. Such coatings have been applied to surgical sutures to improve fiber lubricity, knot snug-down and tie-down performance, and for local delivery of pharmaceutical agents such as antibacterial agents. For example, there has been extensive application of the homopolymer poly(glycolic acid) (see for example U.S. Pat. No. 3,277,003) and copolymers of glycolic acid with a variety of other monomers which produce absorable polymer (see for example U.S. Pat. No. 3,839,297). Other polymers that have been used to coat sutures include U.S. Pat. No. 5,378,540 (polycaprolactones); U.S. Pat. No. 5,312,437 (poly(oxypropylene)glycol/lactide/glycolide copolymer); U.S. Pat. No. 5,147,383 (polyvinyl esters); U.S. Pat. No. 5,123,912 (poly(alkylene)glycol/lactide/glycolide copolymer); U.S. Pat. No. 5,102,420 (polyetheramide); U.S. Pat. No. 5,100,433 (p-dioxanone/ε-caprolactone copolymer); U.S. Pat. No. 5,032,638 (homopolymer of hydroxy butyrate linkages); U.S. Pat. No. 4,857,602 (triblock polymers of glycolide/poly(alkyleneoxide)/trimethylene carbonate); U.S. Pat. No. 4,844,067 (sucrose fatty esters); U.S. Pat. No. 4,711,241 (glycolic acids): U.S. Pat. No. 4,649,920 (poly(alkylene oxides)); U.S. Pat. No. 4,532,929 (fatty acids); and U.S. Pat. No. 4,433,688 (isocyanate capped polyhydroxylated polyesters).

It has been suggested that several of these biodegradable polymer coatings can theoretically be used to coat sutures and implants with pharmaceutical agents, with the biodegradable polymeric coating providing controlled release of the pharmaceutical agent at the site of surgical intervention. For example, U.S. Pat. No. 5,378,540 describes compositions for coating a surgical suture with a biodegradable polylactone polymeric sheath, optionally containing a pharmaceutical agent. The suture is coated by dipping it in an organic solvent containing the polymer and pharmaceutical agent and allowing the suture to dry.

However, prior art methods for coating sutures and implants have typically been limited with respect to the types of pharmaceutical agents that can be incorporated into the coating sheath. Generally, the pharmaceutical agents must be hydrophobic, as they must be soluble in the organic solvent used to dissolve the polymer prior to coating the suture.

While methods have been developed to coat implants with water soluble pharmaceutical agents, especially antibacterial agents, these methods are not readily adaptable to easily and efficiently coat medical devices with a wide variety of pharmaceutical agents, especially nucleic acids, as they either require complex, expensive machinery or suffer from other undesirable limitations. These methods are also not suitable for providing coatings exhibiting controlled or sustained release of pharmaceutical agents.

For example, U.S. Pat. No. 5,474,797 describes a process for dry-coating implants with bactericidal agents involving depositing a 0.5–10 μm thick layer of bactericidal agent onto the implant in the form of ionized atoms via ion-beam-assisted deposition in a vacuum chamber. In addition to requiring expensive equipment, this method also suffers from the limitation that the pharmaceutical agent to be administered must be readily ionizable. Furthermore, the coated implants do not provide controlled or sustained release of bactericidal agent.

U.S. Pat. No. 4,952,419 describes a method for coating implants with bactericidal agents that involves applying a film of silicone oil to the implant surface followed by contacting the oiled surface with powdered antibacterial agents. While relatively simple, this method requires several manipulations and does not allow for sustained delivery of bactericidal agents. The method also requires that the pharmaceutical agent be available in powdered form.

U.S. Pat. No. 4,024,871 describes sutures impregnated with water soluble antimicrobial agents. The sutures are impregnated by soaking in a dilute solution of antimicrobial agent. The sutures are dried, leaving a residue of antimicrobial agent distributed substantially throughout the suture filament. The suture is then top-coated with polyurethane to prevent the antimicrobial agent from leeching out of the suture. As is readily apparent, this method is not suitable for coating devices that do not readily take up, or become impregnated with, the desired pharmaceutical agent. Furthermore, because the suture is top-coated with polyurethane, this method is not useful for the controlled delivery of pharmaceutical agents at the site of surgical intervention. Rather, the suture is impregnated with an antimicrobial agent to insure its sterility.

Accordingly, there remains a need in the art for compositions and methods which allow medical devices to be easily and efficiently coated with a wide variety of pharmaceutical agents, especially hydrophilic pharmaceutical agents, and that further provide controlled or sustained release of the pharmaceutical agents into the local area surrounding the site of medical intervention.

The prior art methods for coating implants and sutures also typically deposit a sheath or layer of polymer, optionally containing a pharmaceutical agent, tens of microns thick onto the implant or suture. As the biodegradable polymeric coating dissolves, the pharmaceutical agent is released into the area surrounding the implant, where it may be taken up by the surrounding cells. Thus, implants and sutures coated with the prior art compositions and methods deliver pharmaceutical agents extracellularly.

Often times, it is desirable to deliver pharmaceutical agents intracellularly rather than, or in addition to, extracellularly. Such applications are useful where, for example, the pharmaceutical agent cannot easily penetrate or traverse the cellular membrane. Examples of such pharmaceutical agents include oligonucleotides such as antisense DNA and RNA, ribozymes, DNA for gene therapy, transcription factors, growth factor binding proteins, signalling receptors and the like.

Microspheres and/or nanospheres are a widely used vehicle for delivering drugs intracellularly. Generally, microspheres and/or nanospheres comprise a biodegradable polymeric core having a pharmaceutical agent incorporated therein. Microspheres are typically spherical and have an average diameter of about 1 to 900 $\mu$m. Nanospheres are typically spherical and have an average diameter of less than 1 $\mu$m, usually less than about 300 nm.

Advantages of microsphere and/or nanosphere pharmaceutical formulations include their ability to enter cells and penetrate intracellular junctions. Another advantage of microspheres and/or nanospheres is their ability to provide sustained or controlled release of pharmaceutical agents. Thus, microspheres and/or nanospheres provide a means for intracellular as well as extracellular controlled or sustained delivery of pharmaceutical agents.

Accordingly, it would be extremely advantageous to have available methods and compositions for coating medical devices with microspheres and/or nanospheres containing pharmaceutical agents. Such coated devices would facilitate intracellular as well as extracellular local controlled or sustained release of pharmaceutical agents at the site of medical intervention. These devices would be particularly advantageous for delivering drugs that do not readily penetrate or traverse cellular membranes.

Gene therapy is generally understood to refer to techniques designed to deliver nucleic acids, including antisense DNA and RNA, ribozymes, viral fragments and functionally active therapeutic genes into targeted cells (Culver, 1994, *Gene Therapy: A Handbook for Physicians*, Mary Ann Liebert, Inc., New York, N.Y.). Such nucleic acids may themselves be therapeutic, as for example antisense DNAs that inhibit mRNA translation, or may encode therapeutic proteins that promote, block or replace cellular functions.

Perhaps one of the greatest problems associated with current gene therapy strategies, whether ex vivo or in vivo, is the inability to transfer nucleic acids efficiently into a targeted cell population and to achieve a high level of expression of the gene product in vivo. Viral vectors are regarded as the most efficient system, and recombinant replication-defective viral vectors have been used to transduce (i.e., infect) cells both ex vivo and in vivo. Such vectors have included retroviral, adenovirus, adeno-associated viral vectors and herpes viral vectors. While highly efficient at gene transfer, the major disadvantages associated with the use of viral vectors include the inability of many viral vectors to infect non-dividing cells; problems associated with insertional mutagenesis; problems associated with the ability to "turn on" gene expression over time in the few cells that are transfected; potential helper virus production and/or production and transmission of harmful virus to other human patients.

In addition to the low efficiency of most cell types to uptake and expression of foreign nucleic acids, many targeted cell populations are found in such low numbers in the body that the efficiency of transformation of these specific cell types is even further diminished. Therefore, any gene therapy method which increases the efficiency with which nucleic acids are transferred into targeted cells would greatly enhance the overall usefulness of gene therapy protocols.

Recently, it has been discovered that proliferating repair cells active in the wound healing process are surprisingly efficient at taking up and expressing nucleic acids (copending application Ser. No. 08/631,334, filed Apr. 8, 1996 now U.S. Pat. No. 5,962,427). These proliferating repair cells could provide an efficient means for administering gene therapy directly at a surgical or implantation site. It would therefore be extremely advantageous to have available methods and compositions for coating medical devices with a polymeric matrix containing nucleic acids. Such coated devices would provide a convenient means for efficiently transferring therapeutic nucleic acids to proliferating repair cells directly at a wound or site of surgical intervention. The proliferating repair cells would then act as local "bioreactors" for production of therapeutic gene products, such as therapeutic proteins. Of particular significance would be the availability of nucleic acid-coated sutures, as sutures de facto will always be surrounded by injured tissue.

In some circumstances, it may be advantageous for the devices to be coated with microspheres and/or nanosphere containing nucleic acids, as described above. However, transfer of nucleic acids into wounded tissue need not be mediated via microspheres and/or nanospheres.

The difficulty of wound healing and tissue regeneration following surgical intervention is also well documented in the art. In addition, it is well-known that many fragile tissue types, such as normal and diseased liver tissue, tissues in patients suffering from certain metabolic disorders such as diabetes, and tissues that have been irradiated such as tissues following cancer surgery, have difficulty holding sutures.

Currently available wound healing therapies involve the administration of therapeutic proteins. Such therapeutic proteins may include regulatory factors involved in the normal healing process such as systemic hormones, cytokines, growth factors and other proteins that regulate proliferation and differentiation of cells. Growth factors, cytokines and hormones reported to have such wound healing capacity include, for example, the transforming growth factor-$\beta$ superfamily (TGF-$\beta$) of proteins (Cox, D. A., 1995, *Cell Biology International* 19:357–371); acidic fibroblast growth factor (FGF) (Slavin, J., 1995, *Cell Biology International* 19:431–444); macrophage-colony stimulating factor (M-CSF); and calcium regulatory agents such as parathyroid hormone (PTH).

A number of problems are associated with the use of therapeutic proteins in wound healing therapies. For example, the purification and/or recombinant production of therapeutic proteins is often an expensive and time-consuming process. Once purified, most protein preparations are unstable making storage and use cumbersome.

Additionally, because of the short half-life in the body due to proteolytic degradation, repeated administration of high doses of protein are required to ensure that sufficient amounts of the protein reach the tissue.

Finally, for a variety of proteins such as membrane receptors, biological activity is dependant on correct expression and localization in the cell. For many proteins, correct cellular localization occurs as the protein is post-translationally modified. Therefore, such proteins cannot be administered in such a way as to be taken up and properly localized inside the cell.

It would therefore be particularly advantageous to have available medical devices, especially surgical sutures, coated with nucleic acids that stimulate wound healing. Such coated devices would provide for the controlled or sustained release of the nucleic acids into a wound or site of surgical intervention. As described above, proliferating repair cells will take up and express the nucleic acids, thereby stimulating local wound healing.

The coated devices would be particularly useful for difficult surgical situations where compromised wound healing may be a problem, such as surgery in patients having diabetes. Coated sutures would not only enable mechanical juxtaposition of tissues, but through repair cell-mediated nucleic acid transfer would stimulate wound healing along the suture line as well. Illustratively, such sutures would essentially "spot weld" the tissue together. Such sutures would also be useful for re-establishing normal functional tissue architecture at the suture line and in nearby regions.

Nucleic acid-mediated wound healing strategies overcome many of the shortcomings of current wound healing strategies. Unlike proteins, nucleic acids, particularly DNA, are extremely stable for prolonged periods of time under a variety of storage conditions. In addition, since the transfected cells act as bioreactors to produce encoded proteins, administration of even small amounts of nucleic acids would provide therapeutic benefit. Furthermore, since the encoded proteins are expressed in the mammalian cell, they may be post-translationally modified and/or spliced to yield active protein.

As is readily apparent from the above discussion, presently there are no methods and/or compositions available which allow medical devices to be easily and efficiently coated with a wide variety of pharmaceutical agents, especially water-soluble or hydrophilic pharmaceutical agents, that permit local controlled or sustained release of such agents at a site of medical intervention for the treatment of wounds or disease.

There are also presently no methods or compositions available for coating medical devices with microsphere and/or nanosphere pharmaceutical formulations that permit easy and efficient intracellular as well as extracellular local delivery of pharmaceutical agents that do not readily traverse or penetrate cell membranes for the treatment of wounds or disease.

Furthermore, there are currently no compositions or methods available for coating medical devices with nucleic acids, especially nucleic acids that stimulate wound healing, that permit easy and efficient targeted local delivery of nucleic acids in vivo.

Accordingly, these and other deficiencies in the art are objects of the present invention.

3. SUMMARY OF THE INVENTION

These and other objects are afforded by the present invention, which in one aspect provides compositions for coating medical devices with a polymeric matrix containing pharmaceutical agents, especially water-soluble or hydrophilic pharmaceutical agents. The polymeric matrix provides for the controlled or sustained release of pharmaceutical agents at a site of medical intervention. The coated devices are useful for targeted local delivery of pharmaceutical agents for the treatment of wounds or disease.

The coating composition is generally in the form of an emulsion or suspension and comprises at least one biocompatible biodegradable polymer and at least one pharmaceutical agent.

When in the form of an emulsion, the coating composition usually comprises about 0.01% to 15% (w/v), typically about 0.1% to 10% (w/v) and preferably about 1% to 5% (w/v) total polymer, and about 0.001% to 15% (w/v), typically about 0.01% to 10% and preferably about 0.1% to 0.5% (w/v) pharmaceutical agent.

When in the form of a suspension, the coating composition usually comprises about 0.01% to 80% (w/v), preferably about 10% to 30% (w/v), pre-formed or partially formed microspheres and/or nanospheres, and has a viscosity of about 1 to 100 centipoise. Preferably the suspension has a viscosity of about 30 to 50 centipoise. The microspheres and/or nanospheres are comprised of a biocompatible biodegradable polymeric core and have about 0.001% to 30% (w/w) of at least one pharmaceutical agent entrapped, entrained, embedded or otherwise incorporated therein. Preferably, the spheres contain about 1% to 15% (w/w) pharmaceutical agent.

The coating compositions of the invention may further include a propellant for aerosol application.

In a preferred embodiment of the invention, the pharmaceutical agent comprising the coating composition is a nucleic acid.

In another aspect, the present invention relates to methods for coating medical devices with a polymeric matrix containing pharmaceutical agents, especially water soluble or hydrophilic pharmaceutical agents. The methods generally involve preparing a coating composition and coating the medical device with the coating composition. The coating composition may be in the form of an emulsion, suspension or aerosol, as previously described. The composition is applied to the device by any convenient means, including dipping, rolling, brushing, aerosol spraying, etc.

In still another aspect, the present invention relates to medical devices coated with a biocompatible biodegradable polymeric matrix containing at least one pharmaceutical agent. The polymeric matrix coated medical devices are useful for locally delivering pharmaceutical agents to a site of medical intervention for the treatment of wounds or disease. Preferably, the device is coated with a polymeric matrix containing a therapeutically effective amount of pharmaceutical agent.

In one illustrative embodiment, the polymeric matrix coating is in the form of a sheath, encasing the device (or a portion thereof) in a layer of polymeric matrix. When used in a medical procedure, body fluids contact the polymeric matrix sheath, causing it to biodegrade. As the matrix biodegrades pharmaceutical agents are released into the local area surrounding the site of medical intervention. The released pharmaceutical agents are taken up by surrounding cells, where the agents effect therapeutic benefit.

In another illustrative embodiment, the polymeric matrix coating is in the form of microspheres and/or nanospheres, as previously described. When used in a medical procedure, body fluids contact the polymeric matrix coating causing the microspheres and/or nanospheres to biodegrade and release pharmaceutical agents into the local area surrounding the site of medical intervention. In addition, microspheres and/or nanospheres detach from the device. The spheres may be taken up by surrounding cells where they provide controlled or sustained intracellular release of pharmaceutical agents as the spheres biodegrade within the cell.

In a preferred embodiment, the pharmaceutical agent comprising the polymeric matrix coating is a nucleic acid. The nucleic acid-polymeric matrix coating may be in the form of a sheath or microspheres and/or nanospheres, as previously described. When placed in proximity to wounded tissue, such coated devices are useful for locally delivering nucleic acids to cells for, inter alia, local gene therapy. Proliferating repair cells active in the healing process take up the nucleic acids, where they effect therapeutic benefit.

In a particularly preferred embodiment, the nucleic acid is a nucleic acid that stimulates or promotes wound healing. Such coated medical devices exhibit improved wound healing characteristics.

In yet another aspect, the invention relates to methods of locally delivering pharmaceutical agents. The methods generally involve providing a medical device coated with a polymeric matrix containing at least one pharmaceutical agent and using the coated device in a medical procedure. The device is coated with the coating compositions and methods described herein. Preferably, the device is coated with a therapeutically effective amount of pharmaceutical agent.

When used in a medical procedure the polymeric matrix coating the device biodegrades, releasing pharmaceutical agents into the local area surrounding the site of medical intervention, where they may be taken up by surrounding cells and effect therapeutic benefit.

In a preferred embodiment, the methods provide local delivery of nucleic acids into wounded tissues. The preferred methods involve providing a polymeric matrix coated medical device wherein the pharmaceutical agent is a nucleic acid and placing the coated device in or on an area of the body having wounded tissue. As the polymeric matrix biodegrades, proliferating repair cells take up the released nucleic acids, as previously described.

4. BRIEF DESCRIPTION OF THE FIGURES

Figure 2A:
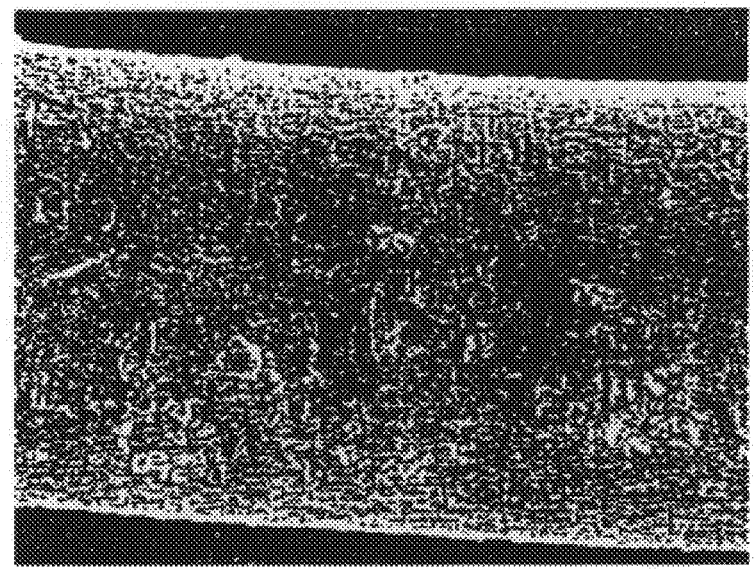
Figure 2B:
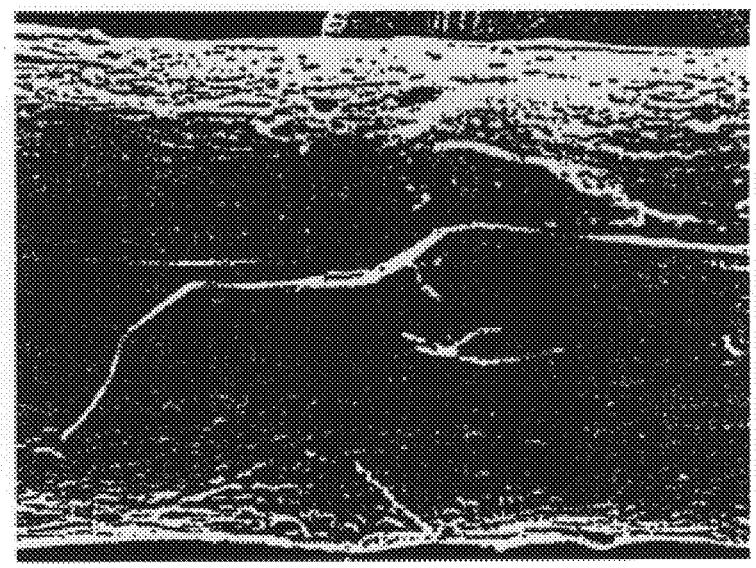
Figure 2C:
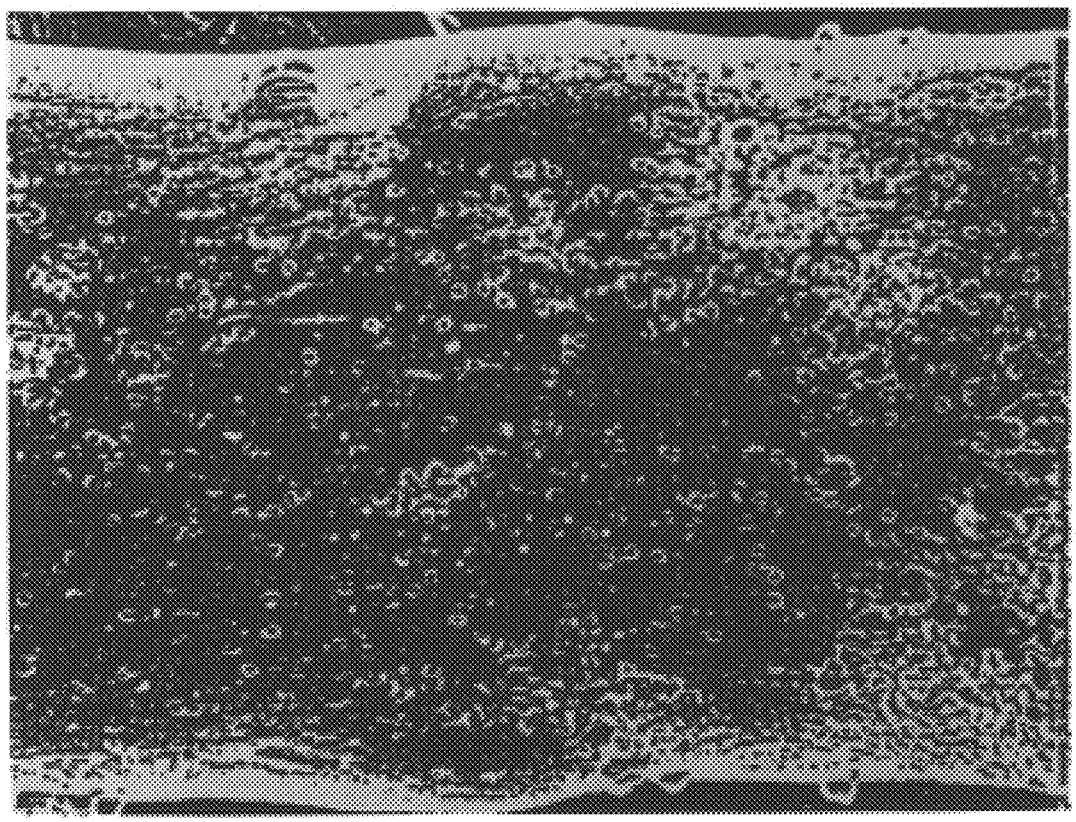
Figure 3A:
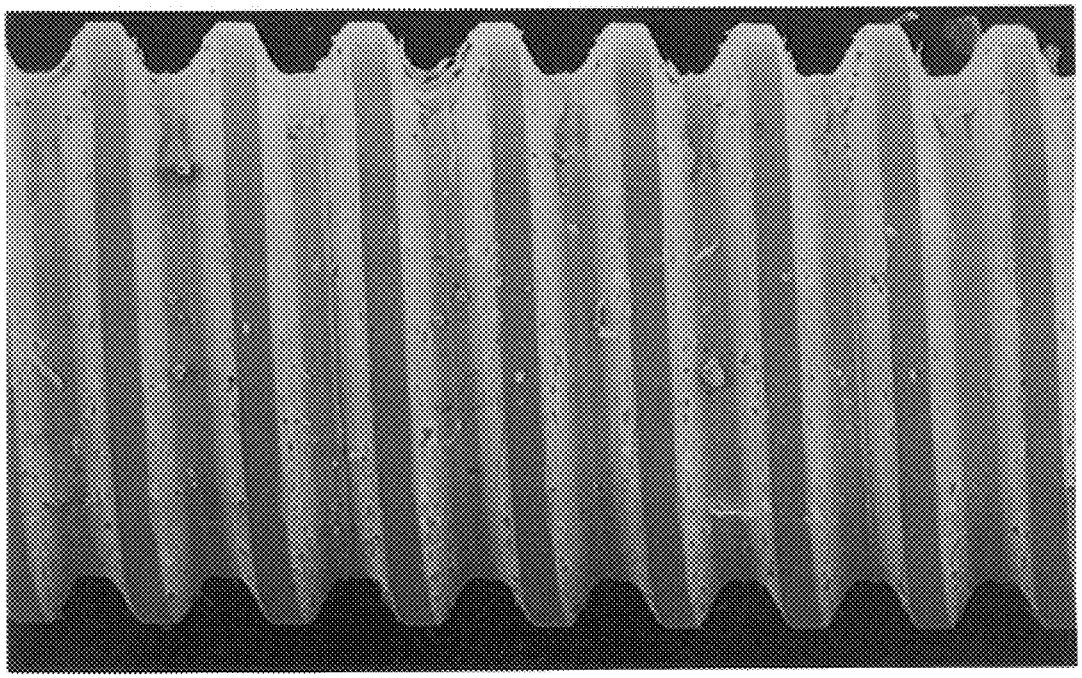
Figure 3B:
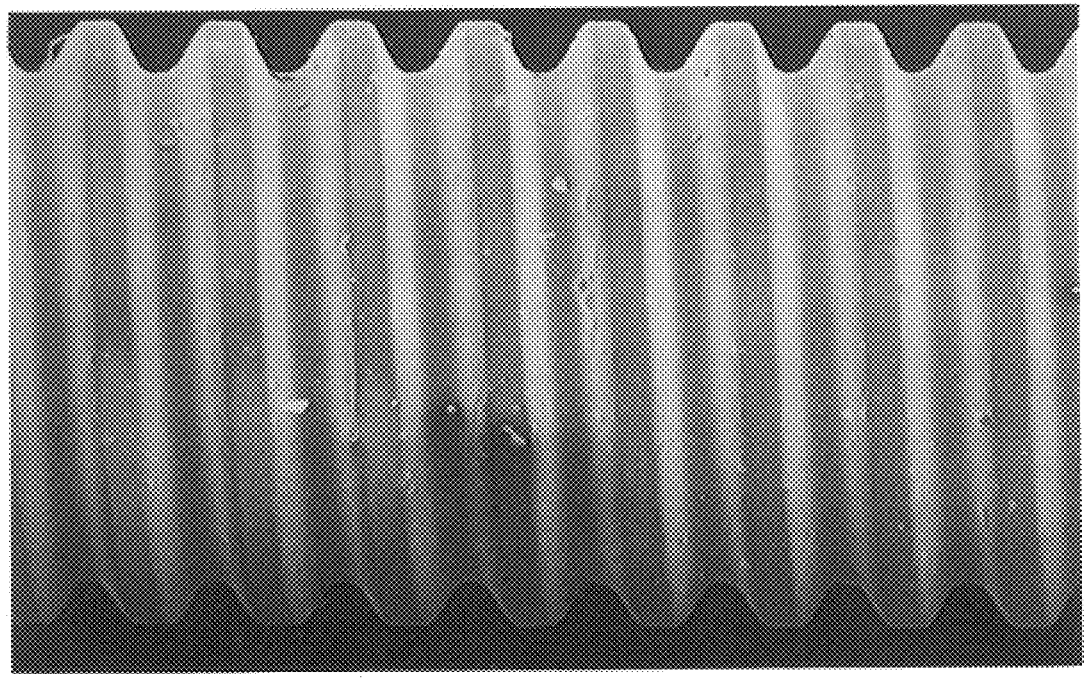
Figure 4A:
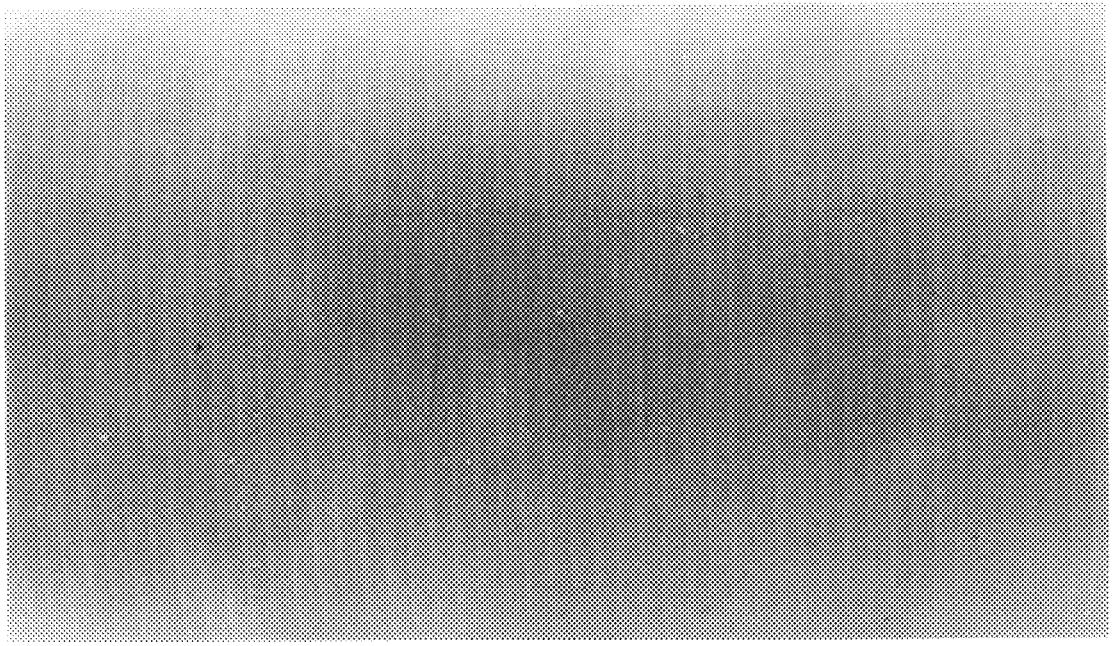
Figure 4B:
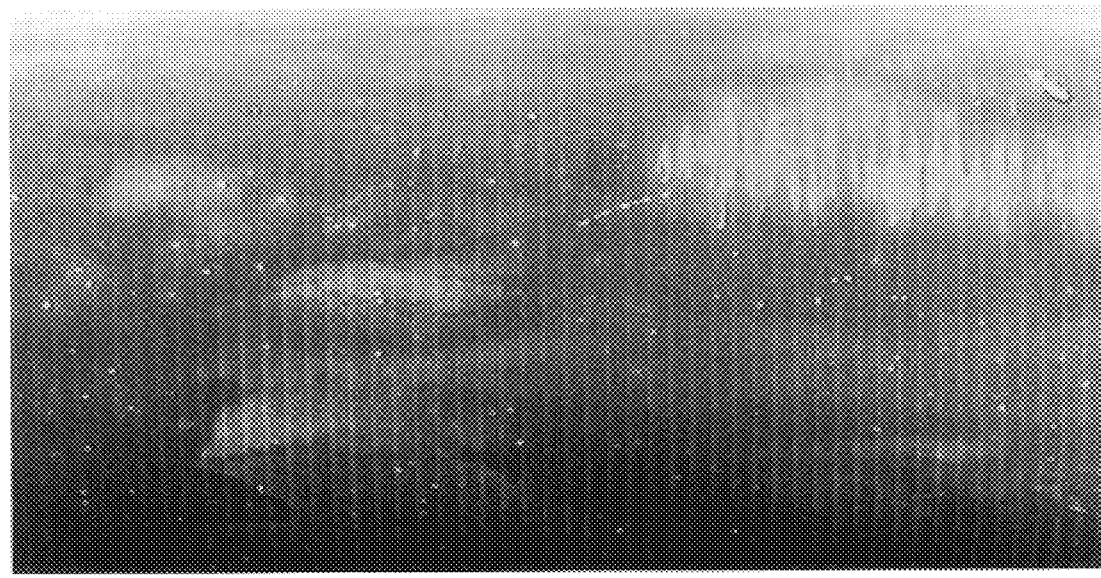
Figure 5A:
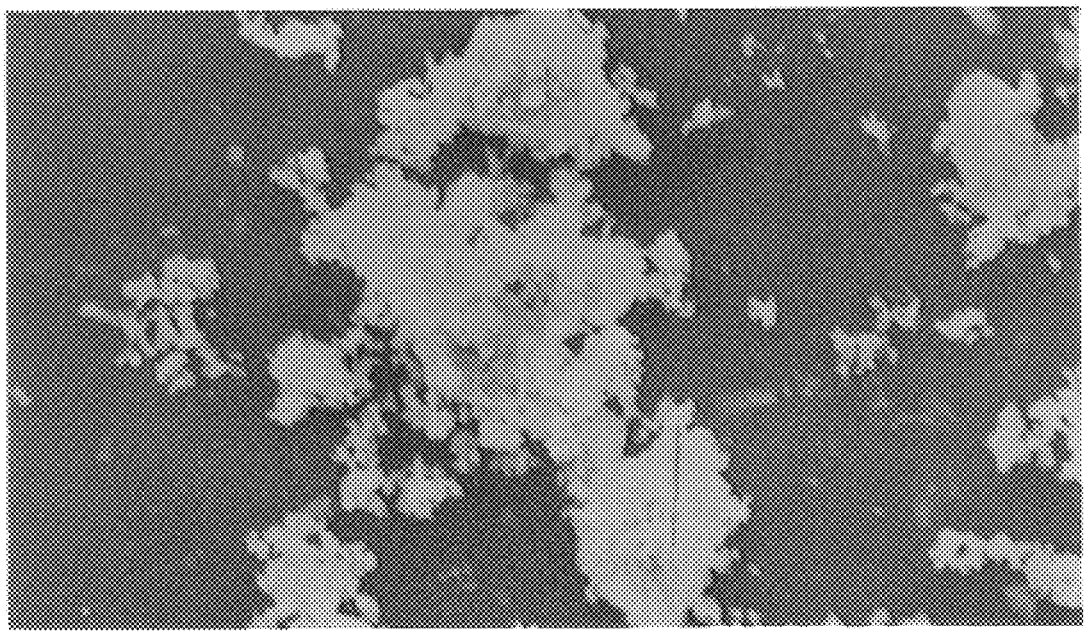
Figure 5B:
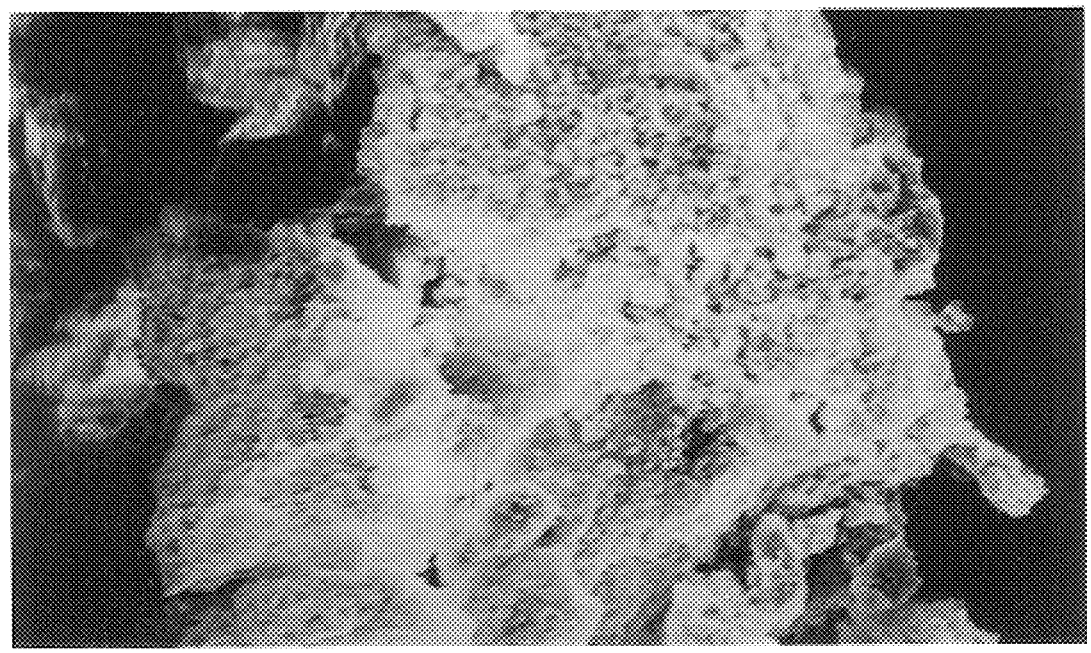
Figure 6:
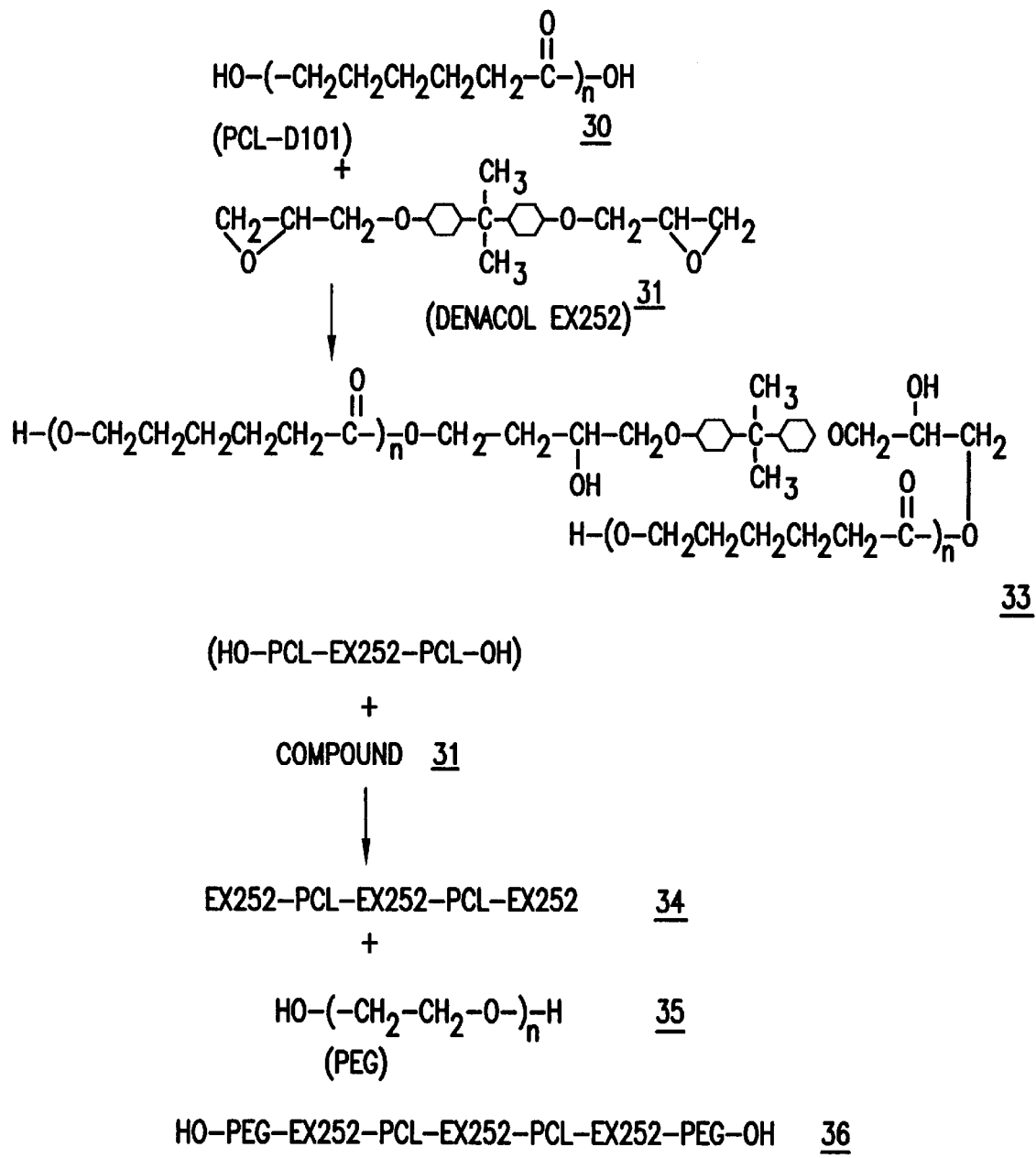

FIG. 1 provides a graph comparing the heat stable alkaline phosphatase activity of tissue repaired with coated sutures and tissue repaired with un-coated sutures;

FIG. 2 provides Scanning Electron Micrographs of coated and uncoated sutures;

FIG. 3 provides Scanning Electron Micrographs of coated and uncoated stainless steel screws;

FIG. 4 provides Scanning Electron Micrographs of coated and uncoated titanium screws;

FIG. 5 provides Scanning Electron Micrographs of coated and uncoated hydroxyapatite-tricalcium phosphate ceramic particles; and FIG. 6 provides an illustrative reaction scheme for the preparation of block copolymers having a hydrophobic PCL segment and a hydrophilic segment.

5. DETAILED DESCRIPTION OF THE PREFERRED EMBODIMENTS 5.1 Definitions

As used herein, the following terms will have the meanings indicated below.

"Medical Device:" As used herein, "medical device" means any device that may be used during medical intervention including, but not limited to, surgical implants, surgical sutures and wound dressings such as bandages.

"Microsphere:" As used herein, a "microsphere" is a generally spherical particle comprised of a biocompatible biodegradable polymeric core having at least one pharmaceutical agent entrapped, entrained, embedded or otherwise incorporated therein. Microspheres generally have an average diameter of about 1 to 900 $\mu$m, typically about 5 to 10 $\mu$m.

"Nanosphere:" As used herein, a "nanosphere" is a generally spherical particle comprised of a biocompatible biodegradable polymeric core having at least one pharmaceutical agent entrapped, entrained, embedded or otherwise incorporated therein. Nanospheres generally have an average diameter of less than about 1 $\mu$m, typically less than about 300 nm. As used herein, "nanosphere" is synonymous with other art-recognized terms for nanometer-sized pharmaceutical formulations such as, for example, "nanoparticle."

"Biocompatible:" As used herein, a material is "biocompatible" if it is suitable for in vivo uses in a human or animal.

Thus a material is biocompatible if it is biologically inert, physiologically acceptable, non-toxic and does not induce adverse biological responses when placed in mammalian tissue.

"Biodegradable:" As used herein, a material is "biodegradable" if it hydrolyses and/or is absorbed into tissues when in contact with tissue and/or tissue fluids.

"Biocompatible Biodegradable Polymeric Matrix:" As used herein, a biocompatible biodegradable polymeric matrix is a material comprised of biocompatible biodegradable polymers in which additional agents, including but not limited to pharmaceutical agents and emulsifying agents, are entrained, entrapped, embedded or otherwise incorporated. Biocompatible biodegradable polymeric matrix specifically includes microspheres and/or nanospheres.

"Pharmaceutical Agent:" As used herein, a pharmaceutical agent is a chemical compound, or combination of compounds, naturally occurring or synthetic, which possesses the property of influencing the normal and/or pathologic behavior of living systems. Pharmaceutical agents include organic molecules, peptides, proteins, nucleic acids and the like. A pharmaceutical agent can be therapeutic, diagnostic, prophylactic, cosmetic, nutritional, etc. A pharmaceutical agent may also be an excipient, filler or adjuvant that acts in conjunction or combination with one or more other pharmaceutical agents.

"Operably Linked:" As used herein, "operably linked" refers to a juxtaposition such that the normal function of the linked components can be performed. Thus, a promoter sequence "operably linked" to a coding sequence refers to a configuration wherein the promoter sequence promotes expression of the coding sequence. The promoter sequence may be constitutive and/or inducible.

"Therapeutically Effective Amount:" A "therapeutically effective amount" of a pharmaceutical agent is an amount effective to provide therapeutic benefit. Thus, for example, for nucleic acids encoding therapeutic proteins, a "therapeutically effective amount" of nucleic acid is an amount effective to provide expressed protein in an amount effective to provide therapeutic benefit.

"Repair Cell:" As used herein, a "repair cell" is any cell which is stimulated to migrate and proliferate in response to tissue injury. Repair cells are a component of the wound healing response. Such cells include fibroblasts, capillary endothelial cells, capillary pericytes, mononuclear inflammatory cells, segmented inflammatory cells and granulation tissue cells.

5.2 The Invention

The present invention relates to compositions for coating medical devices such as, inter alia, surgical implants, sutures and wound dressings, with a biocompatible biodegradable polymeric matrix containing pharmaceutical agents, especially water-soluble or hydrophilic pharmaceutical agents, methods for coating medical devices, and medical devices coated therewith. The coated devices provide for controlled or sustained release of pharmaceutical agents selected to be useful to treat wounds or disease into the local area surrounding the site of medical intervention.

The methods of the invention comprise preparing a coating composition and coating a medical device with the coating composition. Generally, the coating composition is in the form of an emulsion or suspension and comprises at least one biocompatible biodegradable polymer and at least one pharmaceutical agent. When in the form of an emulsion the coating composition is usually comprised of about 0.01% to 15% (w/v), typically about 0.1% to 10% (w/v) and preferably about 1% to 5% (w/v) total polymer, and about 0.001% to 15% (w/v), typically about 0.01% to 10% and preferably about 0.1% to 0.5% (w/v) pharmaceutical agent. In preferred embodiments the emulsion is a water-in-oil ("W/O") emulsion.

When in the form of a suspension, the coating composition is usually comprised of about 0.01% to 80% (w/v), preferably about 10% to 30% (w/v), pre-formed or partially formed microspheres and/or nanospheres and has a viscosity of about 1 to 100 centipoise, preferably about 30 to 50 centipoise. The microspheres and/or nanospheres are comprised of a biocompatible biodegradable polymeric core and have about 0.001% to 30% (w/w), preferably about 1% to 15% (w/w) of at least one pharmaceutical agent entrapped, entrained, embedded or otherwise incorporated therein.

The coating compositions of the invention may further include a propellant for aerosol application. Optionally, the coating compositions may include about 0.1% to 10% (w/v), typically about 1% to 3% (w/v) emulsifying agent and/or about 0.1% to 1% (w/v) of a preservative against microbial contamination.

The composition is applied to the device to deliver a uniform coating and the device allowed to dry. As the device dries, the solvents comprising the coating composition evaporate, depositing a biocompatible biodegradable polymeric matrix containing pharmaceutical agents on the surface of the device. When the device contacts tissue fluids, as when the device is implanted in a patient or used to dress a wound, the polymeric matrix biodegrades, releasing pharmaceutical agents into the local area. Preferably, the polymeric matrix allows for the controlled or sustained release of pharmaceutical agents over prolonged periods of time.

In a preferred embodiment, the compositions and methods of the invention coat medical devices with microspheres and/or nanospheres containing pharmaceutical agents. When the microsphere and/or nanosphere-coated device is placed within or on a patient, the polymeric matrix biodegrades releasing pharmaceutical agents into the local area. Additionally, the microspheres and/or nanospheres detach from the coated device, where they may penetrate into or be taken up by surrounding cells. Thus, devices coated with microspheres and/or nanospheres provide intracellular as well as extracellular controlled or sustained delivery of pharmaceutical agents. This is particularly important for locally delivering pharmaceutical agents that do not readily traverse the cell membrane.

These aspects of the invention are based, in part, on discovery that emulsions suitable for preparing microsphere and/or nanosphere pharmaceutical formulations can be readily adapted to easily, efficiently and durably coat medical devices with a plethora of pharmaceutical agents, particularly water soluble or hydrophilic pharmaceutical agents. The compositions may be used directly or in the form of aerosols to coat a wide variety of medical devices.

Coatings prepared with such compositions are durable in that they are not removed by normal handling of the coated device. Quite surprisingly, it has been discovered that microsphere and/or nanosphere coatings are durable. For example, a polymeric coating comprising sub-micron sized particles did not get stripped from a surgical suture as the suture was passed through skeletal muscle.

The compositions and methods of the invention provide myriad advantages over other current coating techniques. Significantly, the present compositions and methods allow virtually any medical device to be easily and efficiently coated with virtually any pharmaceutical agent, including water-soluble or hydrophilic pharmaceutical agents such as nucleic acids. Thus, the coated medical devices of the invention can be used to locally deliver a wide variety of pharmaceutical agents, alone or in combination, into the local area surrounding a site of medical intervention for the treatment of wounds or disease.

Targeted drug delivery via coated medical devices provides a particularly convenient means for treating wounds or disease. For example, in many instances systemic administration of pharmaceutical agents at therapeutically effective concentrations results in undesirable or toxic side effects. In such instances, targeted local delivery via coated medical devices permits delivery of local concentrations effective to provide therapeutic benefit while avoiding toxicities associated with effective systemic levels of drug. Targeted local delivery via coated medical devices is also advantageous in cases where pharmaceutical agents delivered via other modes of administration do not readily reach the target cell population.

Targeted administration of microsphere and/or nanosphere pharmaceutical formulations via coated medical devices offers myriad advantages over other modes of administering microspheres and/or nanospheres. For example, intravenously delivered microspheres having a size of 4–7 μm are mechanically filtered and retained in the lungs (Troster et al., 1990, *Int. J. Pharm.* 61:85–100). Smaller sized spheres pass through the lungs, but are rapidly taken up by macrophages of the reticuloendothelial system, mainly Kupfer cells of the liver and macrophages of the spleen (Muller et al., 1993, *Int. J. Pharm.* 89:25–31). In many instances, as much as 90% of injected spheres are taken up by the liver and 2–5% are taken up by the spleen and removed from circulation within the five minutes following injection (Muller, 1991, *Colloidal Carriers for Controlled Drug Delivery and Targeting*, Wissenschaftliche Verlagsgesellschaft, Stuttgart). Thus, when administered systemically, many spheres are prevented from reaching their targeted delivery site. By locally administering microspheres and/or nanospheres directly at the site of medical intervention the spheres can be taken up by local surrounding cells, bypassing entry into the blood stream and concomitant sequestration in the lungs, liver and spleen.

In another preferred embodiment, the pharmaceutical agent comprising the compositions of the invention is a nucleic acid. Nucleic acid-coated devices provide targeted controlled or sustained in vivo delivery of nucleic acids to cells surrounding the site of medical intervention for, inter alia, local gene therapy.

This aspect of the invention is based, in part, on the discovery that proliferating repair cells involved in the wound healing process are surprisingly efficient at taking up, and optionally expressing, nucleic acids (copending attorney docket no. 8464-007-999, filed Apr. 8, 1996). These repair cells, which are normally difficult to efficiently transfect both in vitro and in vivo, are extremely efficient at taking up and expressing nucleic acids when induced to proliferate by the wound healing process. The repair cells migrate to a site of tissue injury, infiltrate matrices containing nucleic acids placed at the injury and take up and express the nucleic acids. For example, a collagen sponge containing plasmid DNA encoding mouse BMP-4 (an osteoconductive factor normally expressed by progenitor cells during fracture repair) placed within a 5 mm osteotomy in rats was found to promote bone growth across the gap (id).

A synergistic effect was observed in rats receiving collagen sponges containing two plasmids: one plasmid encoding mouse BMP-4, the other plasmid encoding the PTH1-34 peptide, a 34 amino acid peptide fragment of parathyroid hormone known to interact synergistically with BMP-4 (Ahrens et al., 1993, *J. Bone Min. Res.* 12:871–880).

The present invention capitalizes on these discoveries. Medical devices coated with a polymeric matrix containing nucleic acids provide a convenient means for easy and efficient transfer, and optionally expression, of nucleic acids into proliferating repair cells. For example nucleic acid-coated medical devices placed in proximity to wounded tissue provide an easy and efficient means for transferring nucleic acids to cells for local gene therapy. Coated surgical sutures provide a particularly convenient means of transferring nucleic acids, as the suturing process itself induces tissue injury which in turn induces proliferation of repair cells that can readily take up, and optionally express, the nucleic acids released from the coating.

Virtually any nucleic acid may be taken up by the repair cells, including anti-sense DNA and RNA, plasmid DNA and viral fragments. The nucleic acid itself may be therapeutic, or it may encode therapeutic proteins. Preferably, the device is coated with an amount of nucleic acid effective to provide therapeutic benefit, i.e., an amount effective to achieve an intended effect, such as, inter alia, amelioration or treatment of disease, amelioration of symptoms associated with disease, stimulation or promotion of wound healing, etc. For nucleic acids that are themselves therapeutic, such as for example anti-sense DNAs and RNAs, a therapeutically effective amount refers to an amount of antisense DNA or RNA effective to provide therapeutic benefit. For nucleic acids encoding therapeutic gene products, a therapeutically effective amount refers to an amount of nucleic acid that, when expressed, provides an amount of gene product effective to provide therapeutic benefit. A person skilled in the medical arts could readily determine a therapeutically effective amount without undue experimentation.

Since the uptake and expression of nucleic acids by repair cells requires repair cell proliferation induced by tissue injury, it is understood that devices coated with the nucleic acid-polymer compositions of the invention are to be placed in proximity to tissue where a fresh wound is present. As will be readily apparent to those having ordinary skill in the art, while it may be advantageous to coat medical devices with microspheres and/or nanospheres containing nucleic acids so that the microspheres and/or nanospheres may facilitate intracellular delivery, for delivery of nucleic acids into wounded tissues microspheres and/or nanospheres are not required. The proliferating repair cells efficiently take up nucleic acids delivered into the extracellular matrix.

Locally delivering nucleic acids via coated medical devices overcomes many of the problems associated with currently available in vivo and ex vivo gene therapy protocols. For example, in vivo methods for gene therapy require some form of targeting which, very often does not work. For the coated devices of the invention targeting is not a problem—the nucleic acid in the matrix serves as "bait" that is only taken up by cells that participate in the wound healing process and are resident at the wound site. Ex vivo gene therapy often requires a source of target cells that is either unavailable or resistant to transduction. For coated devices of the invention transduction is not a problem—nucleic acids are efficiently taken up by proliferating repair cells active in the wound healing process.

In a particularly preferred embodiment of the invention, the nucleic acid stimulates or promotes wound healing. Such a nucleic acid may itself be therapeutic or may encode therapeutic gene products that stimulate or promote wound healing in vivo. Preferably, the nucleic acid is a DNA molecule having a promoter sequence operably linked to a DNA sequence encoding therapeutic proteins that stimulate wound healing.

Medical devices coated with nucleic acids that stimulate or promote wound healing will generally exhibit improved healing characteristics. For example, orthopedic surgical implants, such as pins commonly used to set broken or fractured bones, coated with nucleic acids that stimulate wound healing will accelerate bone tissue regeneration in addition to providing mechanical juxtaposition of the injured bone.

Sutures coated with nucleic acids that stimulate or promote wound healing also exhibit improved healing properties. Such coated sutures, in addition to providing mechanical juxtaposition of healing tissues, will stimulate or promote tissue healing through transfer, and optionally expression, of nucleic acids that stimulate or promote wound healing to proliferating repair cells in proximity of the suture line. Illustratively, by stimulating wound healing around the suture, such sutures essentially "spot weld" the suture to the tissue. The coated sutures are particularly useful for suturing fragile or damaged tissues such as normal or diseased liver tissue, tissue that has been irradiated, and tissue in patients suffering from metabolic disorders such as diabetes.

One particularly important feature of the preferred embodiment is that the repair process may be engineered to result in either the formation of scar tissue or tissue regeneration. For example, overexpression of therapeutic proteins at a wound or surgical site may result in regeneration of the injured tissue without formation of scar tissue. In many instances, such as in the case of bone repair, such regeneration is desirable because scar tissue is not designed to support normal mechanical function.

For sutures, it may be desirable to form scar tissue to hold inherently weak tissues together, as previously discussed.

Alternatively, in many instances the formation of scar tissue around a suture is undesirable. Such instances include, for example, ocular surgery, where formation of corneal scar tissue may result in blocked vision.

Thus, the compositions and methods of the invention may be used to coat medical devices with nucleic acids that stimulate wound healing either with or without the formation of scar tissue, depending on the type and level of gene products expressed.

The present compositions, methods and coated devices overcome many of the shortcomings in the art involving wound therapy. First, unlike proteins, high doses of nucleic acids, which are both stable and non-toxic, can be safely administered in vivo. Second, repeated administration, while possible, is not required. The cells which take up and express the nucleic acids act as local bioreactors to provide a continuous supply of encoded gene product at the site of the wound. Third, the nucleic acids can be delivered in a way that addresses the temporal requirements of dosing.

5.3 Coating Compositions

According to the present invention, a novel process has been discovered which makes it possible to adapt compositions commonly used in the art for preparing microsphere and/or nanosphere pharmaceutical sustained release dosage formulations to coat medical devices such as, inter alia, implants, sutures and wound dressings, with a biocompatible biodegradable polymeric matrix containing pharmaceutical agents. The coated devices provide controlled or sustained local delivery of the pharmaceutical agents.

Contrary to the coating compositions and methods described in the literature, which are suitable only for coating medical devices with hydrophobic pharmaceutical agents, the present methods and compositions are suited for coating devices with a wide variety of pharmaceutical agents, whether hydrophilic or hydrophobic in nature.

Generally, the coating compositions of the invention comprise at least one biocompatible biodegradable polymer and at least one pharmaceutical agent. In one embodiment of the invention the coating composition is in the form of an emulsion. One of the advantages of the present invention is that any of the prior art emulsions used to prepare microsphere and/or nanosphere pharmaceutical formulations may be adapted to coat medical devices. Such emulsions include, by way of example and not limitation, water-in-oil emulsions ("W/O"), water-in-oil-in-water ("W/O/W") emulsions, and co-solvent emulsions. Methods of preparing such emulsions are known in the art, for example, as described in U.S. Pat. No. 5,478,564 to Wantier et al.; European Patent Application EP 190,833 to Yamamoto et al.; U.S. Pat. No. 5,480,656 to Okada et. al.; and Allemann et al., 1992, *Intl. J. Pharmaceutics* 87:247–253. Of course, it will be recognized that the type of emulsion prepared will depend in part on the properties of the pharmaceutical agent to be incorporated into the polymeric matrix.

In a preferred embodiment, the coating compositions of the invention comprise a W/O emulsion. While it is to be understood that any methods of preparing W/O emulsions are specifically contemplated by the invention, a typical W/O emulsion may be prepared by emulsifying an organic phase with an aqueous phase to yield an emulsion that appears milky.

For hydrophobic pharmaceutical agents the organic phase comprises at least one polymer and at least one hydrophobic pharmaceutical agent dissolved in an organic solvent that is immiscible with water. Thus, for hydrophobic pharmaceutical agents, coating compositions of the invention may be prepared by dissolving at least one polymer and at least one pharmaceutical agent in a water-immiscible organic solvent to yield an organic phase and emulsifying the organic phase with an aqueous phase to yield a milky emulsion.

As will be readily appreciated by those having skill in the art, one of the advantages of coating medical devices with hydrophobic pharmaceutical agents using emulsions is the reduced residual organic solvent content of the coating as compared to coatings achieved with prior art compositions and methods. Thus, medical devices coated with the compositions and methods of the present invention are less toxic than medical devices coated with prior art compositions and methods. This is especially important when the organic solvent is a toxic solvent such as methylene chloride. Notwithstanding this advantage, since the compositions of the invention are intended for application in humans and animals, water-immiscible organic solvents exhibiting low toxicity are preferred.

In another preferred embodiment of the invention, the pharmaceutical agent is water-soluble or hydrophilic. For hydrophilic pharmaceutical agents the organic phase comprises at least one biodegradable biocompatible polymer dissolved in a water-immiscible organic solvent and the aqueous phase comprises at least one water soluble or hydrophilic pharmaceutical agent dissolved in water.

Thus, for water-soluble or hydrophilic pharmaceutical agents, the coating compositions of the invention may be prepared by dissolving at least one biocompatible biodegradable polymer in a water-immiscible organic solvent to yield an organic phase, dissolving at least one water-soluble or hydrophilic pharmaceutical agent in water to yield an aqueous phase and emulsifying the organic phase with the aqueous phase to yield a milky emulsion.

The aqueous phase may further comprise other agents that enhance the stability of the pharmaceutical agent in water, as will be apparent to those having skill in the art. For example, the aqueous phase may further comprise pharmaceutically acceptable buffering agents for adjustment or maintenance of pH; salts; and the like.

Since the compositions of the invention are intended for human or animal application, they also may contain from about 0.1% to about 1% (w/v) of a preservative against microbial contamination. Such agents include, by way of example and not limitation, methylparaben, ethylparaben, propylparaben, butylparaben, imidurea, quaternium 15, sorbic acid, 2-bromo-2-nitropropane-1,2-diol, dehydroacetic acid, benzoic acid, benzalkonium chloride, benzethonium chloride, phenoxyethanol, benzyl alcohol, cetylpyridinium chloride and chlorobutanol.

Optionally, the aqueous phase may further comprise one or a plurality of emulsifying agents. Such agents are useful to adjust the viscosity of the coating compositions, as will be discussed further below. When present, the emulsifying agent will generally comprise about 0.1% to 10% (w/v) and preferably about 1% to 3% (w/v) of the aqueous phase.

Suitable emulsifying agents useful in the present invention include, by way of example and not limitation, fatty alcohols such as polyvinyl alcohol, lauryl alcohol, myristyl alcohol, cetyl alcohol, stearyl alcohol and oleyl alcohol; fatty acids such as lauric acid, myristic acid, palmitic acid, stearic acid, isostearic acid and oleic acid; fatty acid esters such as glycerol monostearate; polyoxyethylene sorbitan fatty acid esters sold commercially under the trademark TWEEN™ (registered trademarks of Hercules Inc., Wilmington, Del.; available from Sigma Chemical Co., St. Louis, Mo.); polyalkylene glycols such as polyethylene glycol; triethanolamine fatty acid esters such as triethanolamine oleate; fatty acid salts such as sodium oleate; sodium dodecyl sulfate (SDS); cellulose acetate; polaxomers such as block copolymers of ethylene oxide and propylene oxide sold under the trademarks PLURONIC F-68™ and PLURONIC F-127™ (registered trademarks of BASF; available from Sigma Chemical Co., St. Louis, Mo.); quaternary ammonium compounds such as didodecyldimethyl ammonium bromide (DMAB); and oils such as mineral oil, petrolatum, cottonseed oil, coconut oil, sesame seed oil, peanut oil, isopropyl myristate and isopropyl palmitate.

Water-immiscible organic solvents useful in the present invention are typically volatile at room temperature, either under reduced air pressure, or more preferably at atmospheric pressure. Suitable water-immiscible solvents include, by way of example and not limitation, chloroform, methylene chloride, ethyl acetate, amyl alcohol, amyl acetate, and the like. Combinations of methylene chloride with acetone, dimethylsulfoxide, acetonitrile and/or tetrahydrofuran may also be used to form an organic phase to dissolve polymer or hydrophobic pharmaceutical agents.

It is to be understood that the choice of water-immiscible organic solvent will depend in part on the stability of the pharmaceutical agents in the solvent. For particularly preferred compositions comprising nucleic acid pharmaceutical agents (discussed in more detail below), the solvent preferably does not induce damage to nucleic acids. Such solvents include, by way of example and not limitation, halogenated hydrocarbons such as methylene chloride; polyhalogenated hydrocarbons such as chloroform; aromatics; halogenated aromatics; and others as will be apparent to ordinarily skilled artisans. Solvents used to prepare particularly preferred compositions will preferably be free of nucleases.

Biocompatible biodegradable polymers useful in the present invention are those typically employed in the art of preparing microsphere and/or nanosphere pharmaceutical formulations. In preferred embodiments, the biocompatible biodegradable polymer will allow for the sustained release of pharmaceutical agents over prolonged periods of time. Suitable polymers include, by way of example and not limitation, polyesters such as polyglycolides, polylactides and polylactic polyglycolic acid copolymers ("PLGA"); polyethers such as polycaprolactone ("PCL"); polyanhydrides; polyalkyl cyanoacrylates such as n-butyl cyanoacrylate and isopropyl cyanoacrylate; polyacrylamides; poly (orthoesters); polyphosphazenes; polypeptides; polyurethanes; and mixtures of such polymers.

It is to be understood that virtually any biocompatible biodegradable polymer that is now known or that will be later developed that is suitable for the sustained or controlled release of pharmaceutical agents may be employed in the present invention.

The choice of polymer will depend on the particular application, pharmaceutical agent to be delivered, and medical device to be coated. Factors to be considered in choosing a particular polymer include the solubility of the polymer in the solvents used to prepare the coating composition, the period of time over which the pharmaceutical agent is to be released, the biocompatibility of the polymer, the ability of the polymer to adhere to the medical device being coated, and other considerations as will be apparent upon review of the disclosure. For sutures, additional considerations include the knot tie-down and snug-down properties of the coated sutures under both wet and dry suturing conditions. An ordinarily skilled artisan will be able to choose a polymer or mixture of polymers suitable for a particular application without undue experimentation.

The compositions will usually comprise about 0.01% to 15% (w/v), typically about 0.1% to 10% (w/v) and preferably about 1% to 5% (w/v) total polymer. The viscosity of the composition will usually be from about 1 to 100 centipoise, preferably about 30 to 50 centipoise, as measured by Otswald viscometer.

In preferred embodiments, the biocompatible biodegradable polymer is a copolymer of glycolic acid and lactic acid ("PLGA") having a proportion between the lactic acid/glycolic acid units ranging from about 100/0 to about 25/75. The average molecular weight ("MW") of the polymer will typically range from about 6,000 to 700,000 and preferably from about 30,000 to 120,000, as determined by gel-permeation chromatography using commercially available polystyrene of standard molecular weight, and have an intrinsic viscosity ranging from 0.5 to 10.5.

The length of the period of continuous sustained or controlled release of pharmaceutical agent from the coated medical devices according to the invention will depend in part on the composition ratio of lactic acid/glycolic acid. Generally, a higher ratio of lactic acid/glycolic acid, such as for example 75/25, will provide for a longer period of controlled or sustained release of pharmaceutical agent, whereas a lower ratio of lactic acid/glycolic acid will provide for more rapid release of pharmaceutical agent. Preferably, the lactic acid/glycolic acid ratio is 50/50.

The length of period of sustained or controlled release is also dependent on the MW of the polymer. Generally, a higher MW polymer will provide for a longer period of controlled or sustained release.

Blends of low and high MW polymers may also be employed to control the release kinetics of pharmaceutical agents. Such blend ratios can range from about 5/100 of low MW polymer/high MW polymer to about 50/50 of low MW polymer/high MW polymer.

Compositions comprising particular polymer ratios, polymer MWs and polymer blends suitable for a particular application will be apparent to those having skill in the art (see, e.g., Bodmer et al., 1992, *J. Controlled Release* 21:129–138).

The coating properties of the compositions of the invention are affected by the volumetric ratio of the organic phase to aqueous phase comprising the composition. Compositions suitable for most coating applications will generally comprise about 55% to 99.9% (v/v), typically about 75% to 95% (v/v) and preferably about 80% to 90% (v/v) organic phase. These ratios correspond to a viscosity range of about 1.5 to 3.5 poise.

The concentration of pharmaceutical agent comprising the coating composition may also affect its coating properties. In addition, it may affect the amount of pharmaceutical agent incorporated into the polymeric matrix. While it will be appreciated that the amount of pharmaceutical agent that can be incorporated into the coating composition will depend on the MW of the pharmaceutical agent and its solubility in the solvents, it has been found that compositions comprising about 0.001% to 15% (w/v), typically about 0.01% to 10% (w/v) and preferably about 0.1% to 0.5% (w/v) pharmaceutical agent provide suitable coatings.

Generally, the coating composition will be emulsified to achieve an emulsion that appears milky. Any suitable means may be used to achieve the milky emulsion including, by way of example and not limitation, vigorous stirring, vortexing and sonication. Of course, the method selected to achieve the milky emulsion will depend in part upon the stability of the pharmaceutical agent to the emulsification method, as will be apparent to those having ordinary skill in the art. Vortexing the coating composition for about one minute followed by sonicating the composition for about 30 seconds at about 0° C. using a probe-type sonicator reproducibly yields a very milky and stable emulsion satisfactory for most coating applications.

Particularly preferred compositions comprising nucleic acid pharmaceutical agents (discussed in more detail below) may also be prepared using vortexing, homogenization or sonication. There is significant literature suggesting that applying high shear forces to nucleic acids, especially plasmid and chromosomal DNAs, via vortexing, homogenization or sonication causes significant damage to the DNA (see, e.g., Kondo et al., 1985, *Radiation Research* 104:284–292; Miller et al., 1991, *Ultrasound in Medicine and Biology* 17:729–735; Miller et al., 1991, *Ultrasound in Medicine and Biology* 17:401–406; Nicolau et al., *Methods in Enzymology* 149:157–175). Quite surprisingly, however, it has been discovered that applying high shear forces via vortexing or sonication to coating compositions of the invention containing nucleic acid pharmaceutical agents does cause significant damage to the nucleic acids. For example, while sonicating plasmid DNA in absence of polymer caused significant damage to the DNA, sonicating a plasmid DNA-polymer composition in the emulsion form of the invention did not cause significant damage to the DNA (see, e.g., Example 6 demonstrating expression of sonicated plasmid DNA). Accordingly, coating compositions of the invention containing nucleic acid pharmaceutical agents, especially DNAs, can be prepared using vortexing, homogenization, and sonication as described above without causing significant damage to the nucleic acid. It is also likely that other procedures used for formulating emulsion in pharmaceutical preparations could also be used for making emulsion containing nucleic acids.

In an alternative embodiment, a co-solvent system may be used to prepare the W/O emulsion for coating medical devices with hydrophilic and/or semi-polar pharmaceutical agents. In this alternative embodiment the organic phase of the W/O emulsion comprises at least one biocompatible biodegradable polymer and at least one semi-polar and/or hydrophilic pharmaceutical agent dissolved in a co-solvent comprising a water-immiscible organic solvent and a water-miscible organic solvent. The coating composition is prepared by:

(a) dissolving at least one biodegradable biocompatible polymer in a water-immiscible organic solvent;

(b) dissolving at least one hydrophilic and/or semi-polar pharmaceutical agent in a water-miscible organic solvent;

(c) admixing the solutions from steps (a) and (b) to yield an organic phase; and (d) emulsifying the organic phase with an aqueous phase to yield a milky emulsion.

The aqueous phase may optionally contain antimicrobial agents and emulsifying agents, as described above.

Typical water-immiscible organic solvents are those previously described. Suitable water-miscible organic solvents will yield a co-solvent system with water having a low vapor pressure so that it evaporates at low temperature and pressure. Preferably, the water-miscible solvent will be semi-polar, non-toxic and will not damage the pharmaceutical agent. Suitable water-miscible solvents include, by way of example and not limitation, acetone, acetonitrile, ethanol, dimethyl acetamide (DMA), tetrahydrofuran (THF), dioxane, dimethylsulfoxide (DMSO) and dimethylformamide (DMF).

The water-miscible organic solvent is put in proportion relative to the water-immiscible organic solvent such that there is no precipitation of the polymer in the aqueous phase. If the amount of the water-miscible organic solvent is too high an emulsion is not obtained. The organic phase and the aqueous phase become miscible and the polymer precipitates in the aqueous phase.

An emulsion is achieved with ratios of water-miscible organic solvent to water-immiscible organic solvent ranging from about 5/95 up to about 70/30 by volume. The minimum proportion of water-miscible organic solvent relative to water-immiscible organic solvent is linked to the desired level of incorporation of pharmaceutical agent into the polymeric matrix. The minimum proportion will therefore depend on the particular application and will be apparent to those having skill in the art.

In another embodiment, the coating compositions of the invention may be formulated as aerosols for aerosol spray application. Methods for preparing and dispensing aerosols are well known in the art (see, e.g., Lachman et al., 1976, "Pharmaceutical Aerosols," In: *The Theory and Practice of Industrial Pharmacy* 270–295 (Lea & Febiger, Philadelphia, Pa.); *U.S. Pharmacopeia National Formulary* 23/NF 18:1760–1767 (1995); Ansel et al., 1995, "Aerosols, Inhalations and Sprays," In: *Pharmaceutical Dosage Forms and Drug Delivery Systems* 443–459 (Lea & Febiger, Philadelphia, Pa.).

Aerosol compositions of the invention are essentially W/O emulsions, as previously described, further comprising a liquified propellant. The liquified propellant can be any pharmaceutically acceptable liquified propellant having a vapor pressure alone or in mixture from about 20 p.s.i.g. to about 130 p.s.i.g. and is preferably selected from the group consisting of propane, butane, isobutane, dichlorodifluoromethane, monochlorodifluoromethane, dichlorotrifluoroethane, monochlorotetrafluoroethane, tetrafluoroethane, dichloromonofluoroethane and difluoroethane.

The aerosol compositions of the invention may be prepared by charging a coating composition of the invention with a liquified propellant into an aerosol dispenser. The aerosol dispenser can be any conventional aerosol can or bottle or other appropriate container, as are well known in the art.

In another embodiment of the invention, the coating composition is in the form of a suspension and comprises pre-formed or partially-formed microspheres and/or nanospheres suspended in a suitable solvent. Such compositions are particularly suited for coating medical devices with microsphere and/or nanosphere coatings, as will be described more thoroughly below.

Suspensions suitable for coating a device with microspheres and/or nanospheres typically will have fluid properties that allow formation of a uniform coating, and will generally comprise about 0.01% to 80% (w/v), preferably about 10% to 30% (w/v) microspheres and/or nanospheres, depending on the viscosity of the solution. Suspensions having a viscosity of about 1 to 100 centipoise, and preferably about 30 to 50 centipoise, will typically yield a uniform coating.

The suspension may optionally include emulsifying agents and antimicrobial agents, as previously described. The suspension may also be formulated as an aerosol, as previously described, for aerosol spray application of microspheres and/or nanospheres onto a medical device.

Microspheres and/or nanospheres comprising the suspension are comprised of a biocompatible biodegradable polymeric core and have at least one pharmaceutical agent entrapped, entrained, embedded or otherwise incorporated therein. Typically, the microspheres and/or nanospheres will comprise about 0.001% to 30% (w/v) pharmaceutical agent, preferably about 1% to 15% (w/v) pharmaceutical agent.

Pre-formed microspheres and/or nanospheres may be prepared using methods commonly employed in the a such as the methods described in U.S. Pat. No. 5,478,564 to Wantier et al.; European Patent Application EP 190,833 to Yamamoto et al.; U.S. Pat. No. 5,480,656 to Okada et. al.; and Allemann et al., 1992, *Intl. J. Pharmaceutics* 87:247–253. Alternatively, microspheres and/or nanopsheres may be obtained by stirring a coating emulsion of the invention for about 18 hours at room temperature to evaporate organic solvents. The spheres are recovered by ultracentrifugation, washed several times with water and dried in a lyophilizer.

Suitable biocompatible biodegradable polymers for preparing microspheres and/or nanospheres are those previously described.

Once formed, the microspheres and/or nanospheres may be suspended in a suitable solvent to prepare the suspension. Solvents useful for preparing suspensions of microspheres and/or nanospheres should not substantially degrade the spheres prior to evaporation of the solvent, and preferably will have a low enough vapor pressure to be easily evaporated at about 25° C. to 30° C. Furthermore, the solvents should not substantially degrade the pharmaceutical agents entrapped in the microspheres and/or nanospheres. Suitable solvents include, by way of example and not limitation, low MW alcohols such as methanol, ethanol, propanol, isopropanol, etc.; acetonitrile; acetone; and co-solvents such as water-acetone, water-acetonitrile, etc. Even water may be used as a solvent; the water can be later removed from the coated device under reduced pressure to hasten evaporation.

To improve adherence of the microspheres and/or nanospheres to the device being coated, the spheres may further include a bioadhesive polymer. The bioadhesive polymer is incorporated into the spheres by adding the bioadhesive to the emulsion used to prepare the microspheres and/or nanospheres. Typically, about 1% to 10% (w/v), preferably about 3% to 5% (w/v), bioadhesive is added to the emulsion used to prepare the spheres.

Alternatively, the coating suspension may further include about 3% to 5% (w/v) bioadhesive polymer. Preferably, the bioadhesive polymer is soluble in the solvents used to prepare the suspension.

Suitable bioadhesive polymers for incorporating into microspheres and/or nanospheres or for including in the coating suspension include, by way of example and not limitation, polaxomers such as block copolymers of ethylene oxide and propylene oxide sold under the trademarks PLURONIC F-68™ and PLURONIC F-127™ (registered trademarks of BASF; available from Sigma Chemical Co., St. Louis, Mo.), methyl cellulose, carbopol, cyanoacrylates, mucin, alginates, acacia, gelatin, collagen and the like.

Optionally, the spheres or coating suspensions may further include pharmaceutical agents that facilitate particulate intracellular DNA and/or RNA processing. Such agents include, by way of example and not limitation, compounds that block or disrupt lysosomal action such as chloroquine, cytochalasin B, colchicine, polyvinylpyrrolidone, sucrose, polylysine, and the like. Such compounds will facilitate gene transfer and entry into the cell nucleus.

Of course, it is to be understood that in many instances it may be desirable to modify the surface of the microspheres and/or nanospheres or to incorporate additional agents into the microspheres and/or nanospheres. For example, it may be desirable to impart the microspheres and/or nanospheres with the ability to target and bind specific tissues or cells, to be retained at the administration site, to protect incorporated pharmaceutical agents, to exhibit antithrombogenic effects and/or to prevent aggregation.

As a specific example, it may be desirable to incorporate receptor-specific molecules, such as for example antibodies, into the microspheres and/or nanospheres to mediate receptor-specific particle uptake. Agents and methods for imparting microspheres and nanospheres with these and additional desirable properties are well known in the art (see, e.g., Troster et al., 1990, *Intl. J. Pharmaceutics* 61:85–100; Davis et al., 1993, *J. Controlled Release* 24:157–163; Muller et al., 1993, *Intl. J. Pharmaceutics* 89:25–31; Maruyama et al., 1994, *Biomaterials* 15:1035–1042; Leroux et al., 1994, *J. Biomed. Materials Res.* 28:471–481). Any of these methods may be used in conjunction with the present invention.

5.4 Pharmaceutical Aaents

One of the main advantages of the coating methods and compositions of the present invention is that they may be used to coat medical devices with virtually any pharmaceutical agent, whether hydrophobic, hydrophilic, polar, semipolar, small molecule, protein, DNA, and the like.

Pharmaceutical agents useful in the present invention include, by way of example and not limitation, cardiovascular agents; agents capable of eliciting an immune response, such as agents commonly found in vaccines; anti-cancer agents; antibiotics; antimicrobial agents; steroidal and non-steroidal anti-inflammatory agents; antiproliferative agents; agents having anti-coagulant characteristic, including anti-thrombin and anti-platelet agents; specific enzyme inhibitors, including nitric oxide synthetase inhibitors (N,N-dimethylarginine), tyrosine kinase inhibitors, alkaline phosphatase inhibitors, angiotensin converting enzyme inhibitors; unique anti-coagulants, including the Tissue Factor Pathway Inhibitor (TFPI) peptide inhibitor; hormones; and the like.

Cardiovascular agents may include simulators such as platelet derived growth factor, endothelial cell growth factor, fibroblast growth factor, smooth muscle cell-derived growth factors, Interleukins 1 and 6, transforming growth factor β, and low density lipoprotein; vasoactive agents such as Angiotensin II, epinephrine, norepinephrine, neuropeptide substances P and K, endothelin, thrombin, leukitrins, prostaglandins, epidermal growth factors, oncogenes (c-myb, c-myo, fos), and proliferating cell nuclear antigen; inhibitors such as transforming growth factor-β, heparin-like factors and vasorelaxants; antithrombins such as heparin, hirudin and hirulog; antiplatelet agents such as aspirin, dipyrimadole, sulfinpyrozone, salicylic acid, eicosapentanoic acid, ciprostene and antibodies to platelet glycoprotein IIb/IIIa; calcium channel blockers such as nifedipine, verapamil, and diltiazem; antitensin converting enzymes (ACE) inhibitors such as captopril and cilazapril; immunosuppressants such as steroids and cyclosporin; fish oils; growth factor antagonists such as angiopeptin and trapidil; cytoskeletal inhibitors such as cytochalasins; anti-inflammatory agents such as dexamethasone,; thrombolytic agents such as streptokinase and urokinase; antiproliferatives such as colchicine and U-86983 (Upjohn Co., Kalamazoo, Mich.); genetic material suitable for DNA and/or anti-sense treatment of cardiovascular disease; protein kinase inhibitors such as staurosporin; smooth muscle migration and/or contraction inhibitors such as cytochalasins, and suramin; and nitric oxide-releasing compounds such as nitroglycerin and analogues thereof.

Agents capable of eliciting an immune response include protein-based bacterial vaccine components such as tetanus toxoid, cholera toxin, Staphylococcus enterotoxin B, pertussis, pneumococcus, Staphylococcus and Streptococcus antigens, and E. Coli (enteropathogenic); and viral vaccine proteins such as AIDS antigens, viral proteins (influenza, adenovirus, etc.), live viruses (attenuated poliovirus, etc.), hepatitis viral components, rotavirus components; viral and bacterial polysaccharides; and DNA-based vaccines.

Anti-cancer agents include alkylating agents such as mechlorethamine, cyclophosphamide, ifosfamide, mephalan, chlorambucil, hexamethylamine, thiotepa, busulfan, carmustine, lomustin, lomustine, semustine, streptozocin, and dicarbaine; antimetabolites such as methotrexate, fluorouracil, floxuridine, cytarabine, mercaptopurine, thioguanine, and pentostatin; natural products such as alkaloids (vinblastine, vincristine, etc.), toxins (etoposide, teniposide, etc.), antibiotics (dactinomycin, daunorubicin, bleomycin, plicamycin, mitomycin, etc.) and enzymes (L-asparaginase, etc.); biological response modifiers such as Interferon-α; hormones and antagonists such as adrenocorticoids (dexamethasone, etc.), progestins, estrogens, anti-estrogens, androgens, and gonadotropin releasing hormone analogues; anti-cancer genes such as tumor suppressor genes (Rb, $p^{53}$, etc.), cytokine genes, tumor necrosis factor-αcDNA, carcinoembryonic antigen gene, and lymphokine gene; toxin-mediated gene therapy; antisense RNA (anti-sense to E6 and E7 genes, etc.); adrenocortical suppressants (mitotane, aminoglutethimide, etc.); and miscellaneous agents such as cisplatin, mitoxantrone, hydroxyurea, and preocarabazine.

Other pharmaceutical agents include enzymes, cytokines, cell adhesion molecules, transport proteins, biologically active peptides, nucleic acids, protamines, collagen, elastin, matrix proteins, carbohydrates, protoglycans, lipids, cholesterols, triglycerides, lipoproteins, apolipoproteins, detergents, and the like.

Of course, the above lists are for illustrative purposes only. Those having skill in the art will recognize that any pharmaceutical agent, or combinations of pharmaceutical agents, that are now known or that will be later developed that can be incorporated into a biocompatible, biodegradable polymeric matrix according to the methods described herein are specifically contemplated by the invention.

5.4.1 Nucleic Acids

In a particularly preferred embodiment, the invention provides coating compositions wherein the pharmaceutical agent is a nucleic acid. Recently, it has been discovered that proliferating repair cells active in the wound healing process are surprisingly efficient at taking up and expressing nucleic acids (copending application Ser. No. 08/631,334, filed Apr. 8, 1996).

Thus, medical devices such as, inter alia, surgical implants, sutures, wound dressings, may be coated with compositions of the invention comprising nucleic acids to provide a convenient means for easily and efficiently transferring, and optionally expressing, therapeutic nucleic acids at the local site of medical intervention. Such coated devices provide a convenient means for targeted delivery of nucleic acids for, inter alia, gene therapy.

The particularly preferred compositions of the invention can be used to coat medical devices with a wide variety of therapeutic nucleic acids. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages.

The term nucleic acid also specifically includes nucleic acids composed of bases other than the five biologically occurring bases (adenine, guanine, thymine, cytosine and uracil).

Nucleic acids useful in the present invention include, by way of example and not limitation, oligonucleotides such as antisense DNAs and/or RNAs; ribozymes; DNA for gene therapy; viral fragments including viral DNA and/or RNA; DNA and/or RNA chimeras; various structural forms of DNA including single-stranded DNA, double-stranded DNA, supercoiled DNA and/or triple-helix DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, *Oligonucleotide Synthesis: A Practical Approach*, IRL Press, Oxford, England). RNAs may be produce in high yield via in vitro transcription using plasmids such as SP65 (Promega Corporation, Madison, Wis.).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH$_2$—S—CH$_2$), dimethylene-sulfoxide (—CH$_2$—SO—CH$_2$), dimethylene-sulfone (—CH$_2$—SO$_2$—CH$_2$), 2'-O-alkyl, and 2'-deoxy-2'-fluoro phosphorothioate internucleoside linkages are well known in the art (see Uhlmann et al., 1990, *Chem. Rev.* 90:543–584; Schneider et al., 1990, *Tetrahedron Lett.* 31:335 and references cited therein).

The nucleic acids may be purified by any suitable means, as are well known in the art. For example, the nucleic acids can be purified by reverse phase or ion exchange HPLC, size exclusion chromatography or gel electrophoresis. Of course, the skilled artisan will recognize that the method of purification will depend in part on the size of the DNA to be purified.

The nucleic acid itself may act as a therapeutic agent, such as for example an antisense DNA that inhibits mRNA translation, or the nucleic acid may encode a variety of therapeutic transcription or translation products that will be expressed by the repair cells. Useful transcription products include antisense RNAs, ribozymes, viral fragments and the like. Useful translation products include proteins such as, for example, membrane proteins, transcription factors, intracellular proteins, cytokine binding proteins, and the like.

In a preferred embodiment of the invention, the nucleic acid is a DNA molecule that encodes gene products that stimulate or promote healing of wounded or damaged tissues in vivo. The DNA molecules may include genomic or cDNAs that code for a variety of factors that stimulate or promote healing, including extracellular, cell surface and intracellular RNAs and proteins. Alternatively, the DNA molecules may encode functional proteins which complement absent or defective gene products arising from genetic defects.

Examples of extracellular proteins include growth factors, cytokines, therapeutic proteins, hormones and peptide fragments of hormones, inhibitors of cytokines, peptide growth and differentiation factors, interleukins, chemokines, interferons, colony stimulating factors, angiogenic factors and extracellular matrix proteins such as collagen, laminin and fibronectin.

Specific examples of such proteins include, but are not limited to, the superfamily of TGF-β molecules including the five TGF-β isoforms and bone morphogenetic factors (BMP), latent TGF-β binding proteins (LTBP), keratinocyte growth factor (KGF), hepatocyte growth factor (HGF), platelet derived growth factor (PDGF), insulin-like growth factor (IGF), the basic fibroblast growth factors (FGF-1, FGF-2), vascular endothelial growth factor (VEGF), Factor VIII and Factor IX, erythropoietin (EPO), tissue plasminogen activator (TPA), activins and inhibins.

Examples of hormones that stimulate wound healing that may be used in the practice of the invention include growth hormone (GH) and parathyroid hormone (PTH).

Examples of cell surface proteins include the family of cell adhesion molecules (e.g., the integrins, selectins, Ig family members such as N-CAM and L1, and cadherins), cytokine signaling receptors such as the type I and type II TGF-β receptors and the FGF receptor and non-signaling co-receptors such as betaglycan and syndecan.

Examples of intracellular RNAs and proteins include the family of signal transducing kinases, cytoskeletal proteins such as talin and vinculin, cytokine binding proteins such as the family of latent TGF-β binding proteins and nuclear trans acting proteins such as transcription factors and enhancing factors.

The DNA molecules may also encode proteins that block pathological processes, thereby allowing the natural wound healing process to occur unimpeded. Examples of blocking factors include ribozymes that destroy RNA function and DNAs that, for example, code for tissue inhibitors of enzymes that destroy tissue integrity, e.g., inhibitors of metalloproteinases associated with osteoarthritis.

One may obtain the DNA segment encoding the protein of interest using a variety of molecular biological techniques, generally known to those skilled in the art. For example, cDNA or genomic libraries may be screened using primers or probes with sequences based on the known nucleotide sequences. Polymerase chain reaction (PCR) may be used to generate the DNA fragment encoding the protein of interest. Alternatively, the DNA fragment may be obtained from a commercial source.

Modified gene sequences, i.e. genes having sequences that differ from the gene sequences encoding the native proteins, are also encompassed by the invention, so long as the modified gene still encodes a protein that functions to stimulate healing in any direct or indirect manner. These modified gene sequences include modifications caused by point mutations, modifications due to the degeneracies of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art. Such modifications include the deletion, insertion or substitution of bases, and thus, changes in the amino acid sequence. Changes may be made to increase the activity of a protein, to increase its biological stability or half-life, to change its glycosylation pattern, and the like. All such modifications to the nucleotide sequences encoding such proteins are encompassed by this invention.

The DNA encoding the transcription or translation products of interest may be recombinantly engineered into a variety of host vector systems that provide for replication of the DNA in large scale for the preparation of coated medical devices. These vectors can be designed to contain the necessary elements for directing the transcription and/or translation of the DNA sequence taken up by the repair cells at the wound in vivo.

Vectors that may be used include, but are not limited to, those derived from recombinant bacteriophage DNA, plasmid DNA or cosmid DNA. For example, plasmid vectors such as pcDNA3, pBR322, pUC 19/18, pUC 118, 119 and the M13 mp series of vectors may be used. Bacteriophage vectors may include λgt10, λgt11, λgt18–23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

Alternatively, recombinant virus vectors including, but not limited to, those derived from viruses such as herpes virus, retroviruses, vaccinia viruses, adenoviruses, deno-associated viruses or bovine papilloma viruses may be engineered. While integrating vectors may be used, non-integrating systems, which do not transmit the gene product to daughter cells for many generations are preferred for wound healing. In this way, the gene product is expressed during the wound healing process, and as the gene is diluted out in progeny generations, the amount of expressed gene product is diminished.

In order to express a biologically active protein, the nucleotide sequence coding for the protein may be inserted into an appropriate expression vector, i.e., a vector which contains the necessary elements for the transcription and translation of the inserted coding sequences. Methods which are well known to those skilled in the art can be used to construct expression vectors having the protein coding sequence operatively associated with appropriate transcriptional/translational control signals. These methods include in vitro recombinant DNA techniques and synthetic techniques. See, for example, the techniques described in Sambrook, et al., 1992, *Molecular Cloning, A Laboratory Manual*, Cold Spring Harbor Laboratory, N.Y. and Ausubel et al., 1989, *Current Protocolsin Molecular Biology*, Greene Publishing Associates & Wiley Interscience, N.Y.

The genes encoding the proteins of interest may be operatively associated with a variety of different promoter/enhancer elements. The promoter/enhancer elements may be selected to optimize for the expression of therapeutic amounts of protein. The expression elements of these vectors may vary in their strength and specificities. Depending on the host/vector system utilized, any one of a number of suitable transcription and translation elements may be used. The promoter may be in the form of the promoter which is naturally associated with the gene of interest. Alternatively, the DNA may be positioned under the control of a recombinant or heterologous promoter, i.e., a promoter that is not normally associated with that gene. For example, tissue specific promoter/enhancer elements may be used to regulate the expression of the transferred DNA in specific cell types.

Examples of transcriptional control regions that exhibit tissue specificity which have been described and could be used include, but are not limited to, elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, *Hepatology* 7:42S–51S); insulin gene control region which is active in pancreatic beta cells (Hanahan, 1985, *Nature* 315:115–122); immunoglobulin gene control region which is active in lymphoid cells (Grosschedl et al., 1984, *Cell* 38:647–658; Adams et al., 1985, *Nature* 318:533–538; Alexander et al., 1987, *Mol. Cell. Biol.* 7:1436–1444): albumin gene control region which is active in liver (Pinkert et al., 1987, *Genes and Devel.* 1:268–276) alpha-fetoprotein gene control region which is active in liver (Krumlauf et al., 1985, *Mol. Cell. Biol.* 5:1639–1648; Hammer et al., 1987, *Science* 235:53–58); alpha-1-antitrypsin gene control region which is active in liver (Kelsey et al., 1987, *Genes and Devel.* 1:161–171); beta-globin gene control region which is active in myeloid cells (Magram et al., 1985, *Nature* 315:338–340; Kollias et al., 1986, *Cell* 46:89–94); myelin basic protein gene control region which is active in oligodendrocyte cells in the brain (Readhead et al., 1987, *Cell* 48:703–712); myosin light chain-2 gene control region which is active in skeletal muscle (Shani, 1985, *Nature* 314:283–286); and gonadotropic releasing hormone gene control region which is active in the hypothalamus (Mason et al., 1986, *Science* 234:1372–1378). Promoters isolated from the genome of viruses that grow in mammalian cells, (e.g., vaccinia virus 7.5K, SV40, HSV, adenoviruses MLP, MMTV, LTR and CMV promoters) may be used, as well as promoters produced by recombinant DNA or synthetic techniques.

In some instances, the promoter elements may be constitutive or inducible promoters and can be used under the appropriate conditions to direct high level or regulated expression of the gene of interest. Expression of genes under the control of constitutive promoters does not require the presence of a specific substrate to induce gene expression and will occur under all conditions of cell growth. In contrast, expression of genes controlled by inducible promoters is responsive to the presence or absence of an inducing agent.

Specific initiation signals are also required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the protein coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

In addition to DNA sequences encoding therapeutic proteins of interest, the scope of the present invention includes the use of ribozymes or antisense DNA molecules that may be transferred into or expressed by the mammalian repair cells. Such ribozymes and antisense molecules may be used to inhibit the transcription of DNA or translation of RNA encoding proteins that inhibit the healing process.

Transferred or expressed anti-sense RNA molecules act to directly block the translation of mRNA by binding to targeted mRNA and preventing protein translation. Transferred or expressed ribozymes, which are enzymatic RNA molecules capable of catalyzing the specific cleavage of RNA may also be used to block protein translation. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of RNA sequences. RNA molecules may be generated by transcription of DNA sequences encoding the RNA molecule.

It is also within the scope of the invention that multiple genes, combined on a single genetic construct under control of one or more promoters, or prepared as separate constructs of the same or different types may be used. Thus, an almost endless combination of different genes and genetic constructs may be employed. Certain gene combinations may be designed to, or their use may otherwise result in, achieving synergistic effects on cell stimulation and regeneration for healing. Any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

5.5 Methods of Preparing Coated Devices

Medical devices such as implants, sutures, wound dressings, etc. may be coated with the coating compositions of the invention using conventional coating techniques as are well known in the art. Such methods include, by way of example and not limitation, dipping the device in the coating composition, brushing the device with the coating composition and/or spraying the device with the aerosol coating compositions of the invention. The device is then dried, either at room temperature or with the aid of a drying oven, optionally at reduced pressure. A preferred method for coating surgical sutures is provided in the examples.

In some cases, the coating compositions of the invention may not adhere well to the device being coated. Such may be the case for orthopedic surgical implants such as titanium pins and other devices constructed of metallic materials. In these cases, it may be desirable to first coat the device with material having an affinity for both the device and the compositions of the invention, and then to further coat the device with the coating compositions of the invention.

The aerosol coating compositions of the invention may be dispensed in the form of a spray or a foam (British Pat. No. 1,372,721), and may form a foam (U.S. Pat. No. 5,378,451) or a gel (U.S. Pat. No. 4,534,958) on the application site. The density of the coating can vary from a few micrometers to millimeters, depending on the dose of the pharmaceutical agent to be delivered.

Applying coating compositions in the form of aerosols is particularly useful for coating medical devices just prior to using the device, such as on-the-spot spraying of surgical implants just prior to implantation or bandages just prior to applying the bandage. This will reduce the possibility of removing the coating through excessive handling.

It is important that the devices be coated with a polymeric matrix containing a pharmaceutically effective amount of pharmaceutical agent, and that the coat be relatively continuous and uniform. To achieve a pharmaceutically effective uniform coating, the device may be coated several times, typically with drying in between each application of coating composition. Thus, for example, the device may be dipped several times in a coating composition, or sprayed several times with a coating composition. The coating process may be repeated as many times as is required to coat the device with a pharmaceutically effective coating.

The number of coats can be varied from a single coat to as many as 100 or more. Typically, the number of coats will be in the range of about 5 to 50, and preferably in the range of about 20 to 30. After each coating, the device is air dried for about 1 to 30 minutes, preferably about 5 to 10 minutes, before applying the next coating.

After applying a sufficient number of coatings the coated device is air-dried for a period of time sufficient to evaporate a substantial amount of the organic solvents. Typically, the device will be air-dried for about 12–48 hours, preferably for about 16–24 hours. Alternatively, the device is dried under reduced pressure, e.g, at about 10 to 400 mmHg, preferably at about 50 to 100 mmHg.

For sutures coated with a polymeric matrix containing plasmid DNA, it has been found that applying a coating composition containing a total of about 0.01 to 10 mg plasmid DNA, and preferably about 1 to 5 mg plasmid DNA, to a 70 cm length of suture using about 5 to 100, preferably about 5 to 50, and more preferably about 15 to 30 coating applications, yields a therapeutically effective and uniform coating.

In a preferred embodiment of the invention a medical device is coated with a polymeric matrix in the form of microspheres and/or nanospheres. Such coated devices, by releasing microspheres and/or nanospheres into the local area surrounding the coated medical device are particularly suited for intracellular as well as extracellular local delivery of pharmaceutical agents.

Coatings comprised of microspheres and/or nanospheres may be obtained with either the emulsion or suspension coating compositions of the invention. While not intending to be bound by theory, it is believed that applying a milky emulsion suitable for the preparation of microspheres and/or nanospheres to a medical device may favor the formation of a polymeric matrix coating comprising micrometer and/or nanometer sized particles rather than the formation of a smooth polymer sheath.

The formation of a polymeric matrix coating comprised of microspheres and/or nanospheres may be facilitated in several fashions. For example, such a polymeric matrix can be facilitated by "nucleating" the formation of microspheres and/or nanospheres in the emulsion coating compositions of the invention prior to coating the device. After the device has been coated, evaporation of residual solvents deposits a coating of microspheres and/or nanospheres containing pharmaceutical agents onto the device.

Microspheres and/or nanospheres may be nucleated by preparing a coating composition wherein the components of the composition are at "critical concentrations" for microsphere and/or nanosphere formation. Such critical concentrations can be achieved by preparing an emulsion coating composition, as previously described, and partially evaporating the emulsion solvents with stirring prior to coating the device. Generally, evaporating about 5% to 60% by volume of the coating composition prior to coating the device yields a composition that favors the formation of microsphere and/or nanospheres when applied to a medical device. Preferably, about 15% to 50% by volume of the composition is evaporated prior to coating the device.

The formation of a polymeric matrix coating comprised of microspheres and/or nanospheres may also be facilitated by first imparting the device to be coated with emulsifier characteristics, as such characteristics are believed to enhance microsphere and/or nanosphere formation. The device can be imparted with emulsifier characteristics by first coating the device with a polymer having emulsifier characteristics, such as polyurethane derivatized with long chain fatty acids (Pitt and Cooper, 1988, *J. Biomed. Res.*:359–382), or other fatty acid-derivatized polymers as are well known in the art. Compositions containing fatty-acid derivatized polymers suitable for coating the device may be prepared by the methods described herein, or by methods known in the art. The device is then coated with the coating compositions of the invention as described herein.

Alternatively, the device can be imparted with emulsifier characteristic by first coating the device with a polymeric matrix containing an emulsifier, and then coating the device with the coating compositions of the invention. Suitable compositions for coating the device with an emulsifier can be prepared by the methods described herein, generally without including a pharmaceutical agent. In this case, the emulsifying agent is typically included in the composition in an amount of about 1% to 10% (w/v), preferably about 1% to 5% (w/v).

In another embodiment, a medical device may be coated with a polymeric matrix comprised of microspheres and/or nanospheres using the coating suspensions of the invention. To coat a device, a coating suspension comprising preformed microspheres and/or nanospheres, prepared as previously described, is used to coat a medical device. Once applied to the device, evaporation of the solvents deposits microspheres and/or nanospheres onto the surface of the device. The device may be coated with multiple applications, as previously described. Adherence of the spheres to the device may be improved by the use of bioadhesives, as previously described.

The microspheres and/or nanospheres may also be covalently attached to the device using chemistries commonly employed in the art of affinity chromatography (see, e.g. BioRad Laboratories, Richmond, Calif. and Pharmacia BioTech, Uppsala, Sweden, products catalogues and references cited therein). Reactive functional groups suitable for covalent attachment of microspheres and/or nanospheres to a device include, by way of example and not limitation, aldehydes, amines, amides, anhydrides, carboxylic acids, epoxides, hydrazides, hydroxyls, thiols and the like.

For covalent attachment, the spheres and the medical device are "activated" to have free reactive functional groups on their surfaces. The spheres and medical device will have complementary reactive groups such that when the medical device is contacted with the spheres under suitable conditions a covalent linkage forms. Such complementary reactive groups include, by way of example and not limitation, epoxides and hydroxyl, amino, sulfhydryl, carboxyl, anhydride and phenol groups; carboxylic acids and hydroxyl or amine groups; and others as will be readily apparent to those having skill in the art of synthetic chemistry. Preferably, the complementary functional groups will react to form covalent linkages under relatively mild conditions.

Generally, activated microspheres and/or nanospheres will be comprised of biocompatible biodegradable polymers having free reactive functional groups, or alternatively, will have incorporated therein or attached thereto an amount of polymer or linker having free reactive functional groups sufficient to allow covalent attachment of the microspheres and/or nanospheres to the device.

Suitable polymers having free reactive functional groups are known in the art and include, by way of example and not limitation, PLGA, polyacrylic acid, poly(sodium acrylate), polyalkylacrylic acid, poly(sodium alkylacrylate), poly (alkylene oxide), polystyrene sulfonic acid, polystyrene carboxylic acid and the like (available from Polymer Source, Inc., Dorval, Quebec, Canada). Suitable linkers having free reactive functional groups are well known in the art of affinity chromatography, as well as other arts.

Typically, when incorporated into or attached to the spheres, an amount of linker or polymer that does not affect the controlled release properties of the microspheres and/or nanospheres is preferred. Generally, the microspheres and/or nanospheres will contain about 0.1% to 10% (w/w), preferably about 1% to 5% (w/w), polymer or linker having free reactive functional groups.

In one embodiment, the microspheres and/or nanospheres are comprised of, or have incorporated therein in an amount suitable for covalent attachment to a medical device, a hydroxy-terminated or epoxide-terminated poly($\epsilon$-caprolactone)-polyether multiblock copolymer (described in copending U.S. Ser. No. 08/389,893, filed Feb. 16, 1995, particularly at pp. 76–96, the disclosure of which is incorporated herein by reference). Hydroxy-terminated or epoxide-terminated poly($\epsilon$-caprolactone)-polyether multiblock copolymers are comprised of hydrophilic segments, which may be a hydrophilic polyether such as poly(ethylene glycol), and hydrophobic poly($\epsilon$-caprolactone) ("PCL") segments.

Block copolymers containing a hydrophobic PCL segments and hydrophilic segments may be synthesized by multiple reactions between hydroxyl end groups and epoxide groups, as illustrated in FIG. 6. The illustrative reaction scheme of FIG. 6 can be used to chemically link copolymer blocks in ABA-, BAB-, as well as $(AB)_n$-type block copolymers such that the hydrophobicity and MW of the block copolymers can be tailored as desired.

Referring to FIG. 6, compound 30 is polycaprolactone diol ("PCL-diol"). The highest MW PCL-diol commercially available has a MW of 3000, which is not high enough to serve as a main segment in a copolymer for sustained release of pharmaceutical agents. In order to obtain a higher MW PCL-diol which will be a solid at the contemplated temperatures of use, PCL-diol (compound 30) is reacted with a polyfunctional epoxide compound (compound 31), such as the difunctional epoxide sold under the trademark DENA-COL EX252™ (Nagasi Chemicals, Osaka, Japan). Using an excess of PCL-diol (about a 2.5:1 molar ratio) yields a polymer chain having PCL-diol as an end group. Reversing the molar ratio yields a polymer having an epoxide end group. The result of the reaction is an expanded PCL-diol, which in the case of FIG. 6 has the structure HO-PCL-EX252-PCL-OH (compound 33).

Epoxide compounds suitable for preparing the block copolymers described herein include epoxide monomers, polyepoxide compounds and epoxide resins. Illustrative bifunctional or polyfunctional epoxide compounds include, but are not limited to, 1,2-epoxides (e.g., ethylene oxide, 1,2-propylene oxide, etc.), alkyldiol diglycidyl ethers (e.g., butanediol diglycidyl ether, Aldrich Chemicals, St. Louis, Mo.), erythritol anhydride, polyfunctional polyglycerol polyglycidyl ethers sold under the trademark DENACOL (Nagasi Chemicals, Osaka, Japan), epichlorhydrin (Alrich Chemical, St. Louis, Mo.), enzymatically-inducible epoxides (Sigma Chemical Co., St. Louis, Mo.) and photopolymerizable epoxides (Pierce, Rockford, Ill.).

Expanded PCL-diol 33 is reacted with excess multifunctional epoxide 31 to achieve end-capping of the expanded PCL-diol 33 with epoxide groups, yielding epoxide-capped compound 34. Referring to FIG. 6, one of the two epoxide groups in difunctional epoxide 31 reacts with the hydroxyl ends of PCL-diol compound 33, leaving the other epoxide group free so that both ends of the PCL-diol are capped with an epoxide group, resulting in an epoxide capped polymer, EX252-PCL-EX252-PCL-EX252 (compound 34).

Compound 34 (Block A) is reacted with excess polyether diol 35 (Block B). In the embodiment illustrated in FIG. 6, polyether diol 35 is polyethylene glycol (PEG; MW 4500). The resulting copolymer is a BAB-type triblock copolymer 36 linked with epoxides and terminated at both ends with hydroxyl groups. An ABA-type triblock copolymer can be formed using excess Block A. Higher order multiblock polymers may be made using ABA- or BAB-type triblock copolymers as reactants (analogous to compound 33) in the general reaction scheme of FIG. 6. A person of ordinary skill can devise a multiplicity of hydroxy- and/or epoxide-terminated block polymers using the techniques described herein.

Of course, other hydrophobic polymers may be used for Block A, including, for example, polylactides, polyglycolides, PLGA, polyanhydrides, polyamino acids and biodegradable polyurethanes. Other hydrophilic polymers suitable for multiblock copolymers include polaxomers such as block copolymers of ethylene oxide and propylene oxide sold under the trademarks PLURONIC F-68™ and PLURONIC F-127™ (registered trademarks of BASF; available from Sigma Chemical Co., St. Louis, Mo.) and poly(alkylene oxides) such as poly(propylene oxide) ("PPO").

In choosing polymers for Blocks A and B a person of ordinary skill in the art would choose an optimal balance of hydrophilic and hydrophobic molecules for a particular application. More hydrophilic polymers will have faster drug releasing properties and vice versa. Other physical properties affecting the release kinetics are those previously described. A person having ordinary skill in the art will be able to choose a balance of desirable properties suited to a particular application without undue experimentation.

The MW of the above-described block copolymers is generally in the range of about 30,000 to 700,000 as measured by gel permeation as previously described. A MW of about 90,000 to 100,000 is preferred. Methods for preparing preferred block copolymers are provided in the Examples.

A significant advantage of forming microspheres and/or nanospheres for covalent attachment to a medical device with the multiblock copolymers described above is their ability to form spheres without the aid of an emulsifying agent. While not intending to be bound by theory, it is believed that when copolymers containing hydrophobic and hydrophilic blocks are added to an aqueous phase, the hydrophilic block will orient towards the aqueous phase and the hydrophobic block will orient towards the center of the emulsion droplet. Thus, a microsphere and/or nanosphere core consisting of a hydrophobic portion with a hydrophilic surface is formed. The outwardly facing hydrophilic segment, such as for example PEG, is a very good emulsifier and will assist in the formation of an emulsion. Moreover, it is believed that the PEG hydrophilic segment will also stabilize the emulsion and prevent aggregation of the emulsion droplets.

In another embodiment, microspheres and/or nanospheres are activated with reactive epoxide groups by covalently attaching a multifunctional epoxide compound to the surface of the spheres. The spheres are prepared using the methods described herein, or conventional means, as previously described. The spheres are comprised of PLGA or any biocompatible biodegradable polymer having a free functional group capable of forming a covalent bond with an epoxide, as previously described, such as for example the hydroxy-terminated poly(ε-caprolactone)-polyether multiblock copolymers described above.

The microspheres and/or nanospheres are contacted with a multifunctional epoxide under conditions conducive to forming a covalent bond between the epoxide compound and the free reactive functional group on the biocompatible biodegradable polymer comprising the spheres. Preferably, the reaction conditions are relatively mild.

For example, the reaction may be carried out in mild conditions by use of a catalyst. Suitable catalysts include, but are not limited to, zinc tetrafluoroborate, tertiary amines, guanidine, imidazole, boron trifluoride adducts (e.g., boron trifluoride-monoethylamine), bisphosphonates, trace metals (e.g., zinc, tin, magnesium, aluminum, etc.) and ammonium complexes (e.g., $PhNH_3^+ AsF_6^-$).

Alternatively, the reaction can be initiated by UV light in the presence of an appropriate catalyst. Suitable catalysts include, but are not limited to, titanium tetrachloride, ferrocene (dicyclopentadieneyliron), zirconocene chloride, carbon tetrabromides and iodoform.

Of course, the actual reaction conditions used may depend on the free reactive functional groups on the biocompatible biodegradable polymer and the pharmaceutical agents contained in the microspheres and/or nanospheres. Suitable reaction conditions are well known in the art of organic chemistry (see, e.g., Streitwieser & Heathcock, *Introduction to Organic Chemistry*, Macmillan Publishing Co., New York, latest edition; Smith, 1994, *Organic Synthesis*, McGraw-Hill, Inc.), and will be readily apparent to those having skill in the art.

Epoxide compounds useful for preparing epoxide activated microspheres and/or nanospheres are those described above.

Preferred methods of preparing epoxide activated microspheres and/or nanospheres suitable for covalent attachment to medical devices are provided in the Examples.

The epoxide-activated microspheres and/or nanospheres are then contacted with an activated medical device under conditions conducive to forming a covalent bond between the epoxide group(s) on the spheres and the free reactive group(s) on the activated medical device, such as the conditions previously described.

The medical device may be activated to have free reactive functional groups by chemically treating the device to derivatize the surface of the device with free reactive functional groups. The chemical treatment methods will depend on the composition of the device, and will be readily apparent to those having skill in the art.

In cases where the device is difficult to derivatize with reactive groups, the device may be activated by coating the device with a coating composition comprising polymers or linkers having free reactive functional groups complementary to the functional groups on the activated microspheres and/or nanospheres. The device is then contacted with activated microspheres and/or nanospheres under conditions wherein the reactive groups on the activated spheres react with the reactive groups on the device, forming a covalent linkage. The coated device may be rinsed to remove excess reagents and dried, as previously described. The device may be coated multiple times, as previously described.

5.6 Medical Devices

The compositions and methods of the invention can be used to coat virtually any medical device. The coated devices will provide a convenient means for local administration of a wide variety of pharmaceutical agents. For example, the compositions of the invention can be used to coat bandages and wound dressings; sutures (degradable and non-degradable); orthopedic protheses such as supporting rod implants, joint protheses, pins for stabilizing fractures, bone cements and ceramics, and tendon reconstruction and prosthetic implants; cardiovascular implants such as heart valve prostheses, pacemaker components, defibrillator components, angioplasty devices, intravascular stents, acute and in-dwelling catheters, ductal arteriosus closure devices, and implants deliverable by cardiac catheters such as atrial and ventricular septal defect closure devices; urologic implants such as urinary catheters; neurosurgical implants such as neurosurgical shunts; ophthalmologic implants such as lens prosthesis, thin ophthalmic sutures and corneal implants; dental prostheses; internal and external wound dressings including bandages and hernia repair meshes; and other devices and implants as will be readily apparent to those having skill in the art.

In a particularly preferred embodiment, the invention provides coated sutures, especially sutures coated with a polymeric matrix containing nucleic acids that stimulate wound healing in vivo. Sutures which may be coated in accordance with the methods and compositions of the present invention include any suture of natural or synthetic origin. Typical suture materials include, by way of example and not limitation, silk; cotton; linen; polyolefins such as polyethylene and polypropylene; polyesters such as polyethylene terephthalate; homopolymers and copolymers of hydroxycarboxylic acid esters; collagen (plain or chromicized); catgut (plain or chromicized); and suture-substitutes such as cyanoacrylates. The sutures may take any convenient form such as braids or twists, and may have a wide range of sizes as are commonly employed in the art.

The advantages of coated sutures, especially sutures coated with a polymeric matrix containing nucleic acids that stimulate wound healing, cover virtually every field of use for sutures in humans and animals.

6. EXAMPLE

PREPARATION AND USE OF A SUTURE COATED WITH MARKER DNA

To demonstrate the feasibility of the coating compositions and methods of the invention, a surgical suture was coated with marker plasmid DNA (encoding human placental alkaline phosphatase) and used to suture rat muscle tissue. The experiment demonstrates successful transfer and expression of DNA in the tissue repaired with the coated suture.

6.1 Preparation of DNA-PLGA Coating Composition

To 1.5 mL of a PLGA/chloroform solution (3% (w/v), 50/50 polylactic polyglycolic acid PLGA co-polymer, ave. MW 90,000, inherent viscosity 1.07) was added 0.2 mL of a solution containing marker plasmid DNA encoding human placental alkaline phosphatase (1 mg DNA, 0.5 mM Tris-EDTA, 0.5 mM EDTA, pH 7.3). The solution was emulsified by vortexing for 2 minutes followed by sonicating for 30 seconds at about 0° C. using a microtip probe-type sonicator at 55 Watts output. This process yielded an emulsion that looked very milky.

6.2 Coating A Surgical Suture

A hole was pierced in a piece of Teflon-coated foil (Norton Performance Plastic Corp., Akron, Ohio) using a 22 gauge needle. On the hole was placed a drop (about 60 μL) of the DNA-PLGA emulsion. A 70 cm length of 3-0 chromic suture (Ethicon) was drawn through the hole to coat the suture. As the suture passed through the hole it became coated with a thin (ca. 30 μm), uniform coating of the coating composition. The suture was allowed to air dry for about 3 minutes, and the coating process repeated 15 times, allowing each coat to air dry.

The coated suture was examined by electron microscopy (150×). Referring to FIG. 2, panel 1 shows an un-coated suture; panel 2 shows a suture coated according to the method described above; and panel 3 shows a coated suture that had been passed through rat skeletal muscle about 25 to 30 times. The black spots in panel 3 are red blood cells that adhered to the suture after passing through the tissue; black spots in panel 3 are blood clots. As is apparent in FIG. 2, the suture was coated with a uniform coating of DNA-PLGA. Furthermore, the coating remained intact even after passing the suture through tissue multiple times.

6.3 Repairing Skeletal Muscle With the Coated Suture

The suture prepared above was sewn into the skeletal muscle tissue of adult male Sprague-Dawley rats using approved protocols and standard methods. The suture exhibited good tie-down properties. One week later, skeletal muscle was harvested, snap frozen in liquid nitrogen and ground into a powder. The powder was incubated in 200 μL lysis buffer, exposed to three freeze-thaw cycles and clarified. The clear liquid was assayed for heat stable alkaline phosphatase activity after incubation at 65° C. using commercially available reagents and protocols (Phospha-Lite™ Chemiluminescent Reporter Assay for Secreted Alkaline Phosphatase, Tropix, Bedford, Mass.). The control group consisted of animals that received uncoated suture. The data are presented in FIG. 1.

6.3.1 Results

As illustrated in FIG. 1, rat skeletal muscle sewn with coated sutures and retrieved after one week exhibited heat stable alkaline phosphatase activity, signifying that the marker alkaline phosphatase gene was expressed in the muscle tissue. Control retrievals showed no significant alkaline phosphatase activity. These data demonstrate that emulsions can be used to effectively coat sutures and deliver genes to proliferating repair cells in vivo.

7. EXAMPLE

PREPARATION OF COATED SCREWS AND CERAMIC PARTICLES

To demonstrate the ability of the coating compositions of the invention to coat a variety of materials a stainless steel screw, titanium screw and hydroxyapatite-tricalcium phosphate ("HTP") ceramic particles were coated with the DNA-polymer emulsion described in the above example.

FIG. 3 shows scanning electron micrographs (with carbon sputtering) of a stainless steel screw before (panel A) and after (panel B) coating. The grooves of the screw clearly have a different contrast before and after coating, demonstrating that the DNA-polymer emulsion covered the grooves with a uniform polymeric coating. General surface defects visible in the uncoated screw were fill in by the DNA-polymer coating.

FIG. 4 shows scanning electron micrographs of a standard orthopedic titanium screw before (pane A) and after (panel B) coating. The coating of the surface is very evident from contrasting electron density of the uncoated screw (panel A) with the relatively darker coated screw (panel B). These results indicate a uniform coating was obtained.

FIG. 5 shows scanning electron micrographs of uncoated HTP ceramic particles (panel A) and coated HTP ceramic particles (panel B). As compared with the highly reflective uncoated particles, coated particles appear less bright and densely covered with a polymeric coating. The DNA-polymer coating allows retention of the particulate formate while uniformly covering the particles with a DNA-releasing polymeric matrix.

8. EXAMPLE

PREPARATION OF A SUTURE COATED WITH MICROSPHERES AND/OR NANOSPHERES CONTAINING MARKER DNA

This example demonstrates a preferred method for preparing epoxide-activated microspheres and/or nanospheres suitable for covalent attachment to a medial device, and methods for covalently attaching the activated spheres to a surgical suture.

8.1 Preparation of DNA-PLGA Microspheres and/or Nanospheres

A DNA-polymer composition is prepared as descried in Example 6.1. The DNA-polymer emulsion is further emulsified with an aqueous solution of polyvinyl alcohol (2.5% w/w, 15 mL, 30,00–70,000 ave. MW PVA) by sonication at 65 Watts for 10 min. at 0° C. to yield a W/O/W emulsion.

The W/O/W emulsion is stirred with a magnetic stirring bar at room temperature for 18 hours to evaporate organic solvent. The spheres are recovered by ultracentrifugation, washed three times with water, resuspended in water by sonication for 30 seconds, and the resultant suspension lyophilized.

8.2 Preparation of Epoxide-Activated Spheres

Lyophilized spheres (8 mg) are suspended in borate buffer (1 mL, 50 mM, pH 5) by sonication for 3 min. Zinc tetrafluoroborate hydrate (2.4 mg) is added to the suspension. A polyfunctional epoxide, DENACOL EX520™ (Nagasi Chemicals, Osaka, Japan) is dissolved in 0.4 mL borate buffer (50 mM, pH 5), and the epoxide solution added to the suspension with stirring at room temp (37° C.). After 30 min., the spheres are recovered by ultracentrifugation, washed three times with water to remove unreacted epoxide, and lyophilized.

8.3 Coating A Surgical Suture

A length of surgical suture is coated with PLGA polymer using the method described in Example 6. Epoxide activated spheres (200 mg) are suspended in borate buffer (1 mL, 50 mM, pH 5) by sonication for 30 seconds. Zinc tetrafluoroborate hydrate (2.4 mg) is added to the suspension. The PLGA-coated suture is coated with the suspension using the method of Example 6.2, or alternatively, by dipping the suture in the suspension. After 30 min. at room temp (37° C.) the suture is rinsed with water and dried. The coating process may be repeated as described in Example 6.2.

8.4 Repairing Skeletal Muscle With the Coated Suture

The microsphere and/or nanosphere coated suture may be used to repair rat skeletal muscle tissue as described in Example 6.3. It is expected that marker DNA will be taken up and expressed by proliferating repair cells.

9. EXAMPLE

PREPARATION OF MULTIBLOCK COPOLYMERS

This example demonstrates methods of preparing preferred hydroxy- or epoxide-terminated multiblock copolymers.

9.1 Preparation of Expanded PCL-diol (Compound 33)

PCL-diol (1.5g, 0.5 mmol, MW 3000, Polyscience, Inc., Warrington, Pa.) was reacted with DENACOL EX252™ (0.21 g, 0.55 mmol, Nagasi Chemicals, Osaka, Japan) in 15 mL THF in the presence of $Zn(BF_4)_2$ catalyst (2% by weight according to epoxide compound) at 37° C. with stirring for 28 hours. To separate the expanded PCL-diol from the non-expanded PCL-diol, gradient precipitation was carried out using heptane and the precipitated, higher MW expanded PCL-diol collected by centrifugation. The product, HO-PCL-EX252-PCL-OH, was washed with 5 mL heptane to remove unreacted epoxide compound and dried.

9.2 Preparation of Compound 34

Compound 33 (0.75 g) was reacted with excess DENACOL EX252™ (0.42 g; molar ratio of Compound 33 to DENACOL EX252™ was 1:4) in 10 mL THF, in the presence of $Zn(BF_4)_2$ catalyst, at 37° C. with stirring for 5 hours. The EX252-PCL-EX252-PCL-EX252 polymer product was precipitated with 30 mL heptane, washed with to mL heptane to remove unreacted epoxide compound and dried.

9.3 Preparation of Compound 36

Compound 34 (1 g) was dissolved in 15 mL THF to which excess polyethylene glycol (PEG) (ave. MW 4500; molar ratio compound 34 to PEG was 1:3) and 20 mg $Zn(BF_4)_2$ catalyst had been added. The reaction proceeded for 48 hours on a shaker table at 37° C. Compound 36 was precipitated with heptane, collected by centrifugation, washed twice with 50 mL water and dried.

9.4 Preparation of Other ABA-Type Triblock Copolymers

Additional ABA-type and BAB-type triblock copolymers were prepared using the general methods described above using the following polyethers as Block A: PEG (ave. MW 4500); the polaxomers PLURONIC F-68™ (F-68) and PLURONIC F-127™ (F-127); and poly(propylene oxide) (PPO). The various polyethers were incorporated into ABA-type and BAB-type triblock copolymers with PCL-diol to obtain polymers having varying hydrophilicity and mechanical properties. PLURONICS™ are diblock copolymers having PPO as the hydrophobic block and poly(ethylene oxide) (PEO) as the hydrophilic block. PF-127 has a MW of about 12,600 and is 70% PPO and 30% PEO. F-68 has a MW of about 6,000 and is 80% PPO and 20% PEO, and hence, is less hydrophilic that F-127. PEG is the most hydrophilic polyether in the group.

The various block copolymers prepared and their respective physical properties are provided in Table 1, below.

TABLE 1

ABA-Type and BAB-Type Triblock Copolymers

| Polymer Type | Morphology | Water Solubility | Film-Forming Properties |
|---|---|---|---|
| PCL/PEG/PCL | crystallizable powder | insoluble | strong, flexible |
| PEG/PCL/PEG | crystallizable powder | swells | flexible, breaks in water |
| PCL/F-68/PCL | crystallizable powder | insoluble | strong, flexible |
| F-68/PCL/F-68 | crystallizable powder | insoluble | flexible |
| PCL/F-127/PCL | crystallizable powder | swells | brittle film |
| PCL/PPO/PCL | sticky wax | insoluble | does not form film |

The "/" marks indicate DENACOL EX252 ™ epoxide linkages

Referring to Table 1, the most useful polymers, from the viewpoint of sustained release of pharmaceutical agents, are copolymers comprised of PCL and PEG or F-68. Polymers which do not crystallize, such as those containing a high level of PPO, have poor mechanical strength and are sticky. Polymers having a large hydrophilic segment, such as the polymer containing PCL and F-127, are difficult to separate from the aqueous phase and will not maintain a solid shape in contact with water or body fluids.

Preferred copolymers are solid at body temperature and are slowly biocompatible and slowly biodegradable in the presence of body fluids.

The present invention is not to be limited in scope by the exemplified embodiments which are intended as illustrations of single aspects of the invention. Indeed, various modifications of the invention in addition to those described herein will become apparent to those killed in the art from the foregoing description and accompanying drawings. Such modifications are intended to fall within the scope of the appended claims.

All patents and publications cited herein are incorporated herein in their entireties for all purposes.

What is claimed is:

1. An in vivo medical treatment device coated with a polymeric matrix, said polymeric matrix comprising at least one biocompatible biodegradable polymer and a pharmaceutically effective amount of at least one nucleic acid.

2. The device according to claim 1, wherein said nucleic acid encodes a gene product that stimulates or promotes wound healing.

3. An in vivo medical treatment device coated with a polymeric matrix, said polymeric matrix comprising a biocompatible biodegradable polymer and a pharmaceutically effective amount of a pharmaceutical agent, wherein the polymeric matrix is in the form of microspheres and/or nanospheres.

4. The device according to claim 1 or 2, wherein the device is selected from the group consisting of surgical implants, surgical sutures and wound dressings.

5. An in vivo medical treatment device coated with a pharmaceutically effective amount of an emulsion comprising a biocompatible biodegradable polymer in an amount of about 0.01% to 15% (w/v) and a nucleic acid in an amount of about 0.01% to 10% (w/v) and having a viscosity of about 30 to 50 centipoise.

6. The device according to claim 5, wherein the device is dried.

7. An in vivo medical treatment device coated with a pharmaceutically effective amount of a suspension comprising about 0.01% to 80% (w/v) microspheres and/or nanospheres and having a viscosity of about 30 to 50 centipoise, wherein the microspheres and/or nanospheres are comprised of a biocompatible biodegradable polymeric core and a nucleic acid in an amount of about 0.01% to 10% (w/w).

8. The device according to claim 7, wherein the device is dried.

* * * * *